(12) United States Patent
Waugh et al.

(10) Patent No.: US 11,141,143 B2
(45) Date of Patent: Oct. 12, 2021

(54) SPINAL IMPLANT SYSTEM AND METHOD FOR LUMBAR AND LUMBOSACRAL FUSION

(71) Applicant: Warsaw Orthopedic, Inc., Warsaw, IN (US)

(72) Inventors: Lindsey G. Waugh, Memphis, TN (US); Anthony J. Melkent, Germantown, TN (US); Jonathan E. Blackwell, Arlington, TN (US); Thomas E. Drochner, Memphis, TN (US); Carrie L. Gowan, Memphis, TN (US); Bret Matthew Wilfong, Hernando, MS (US); Thomas A. Carls, Memphis, TN (US); Richard A. Hynes, Melbourne, FL (US); D. Hal Silcox, III, Atlanta, GA (US); John A. Cowan, Jr., Rome, GA (US); Jean-Pierre Mobasser, Indianapolis, IN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 84 days.

(21) Appl. No.: 16/139,391

(22) Filed: Sep. 24, 2018

(65) Prior Publication Data
US 2019/0021716 A1 Jan. 24, 2019

Related U.S. Application Data

(63) Continuation of application No. 14/494,389, filed on Sep. 23, 2014, now Pat. No. 10,863,976.
(Continued)

(51) Int. Cl.
*A61B 17/02* (2006.01)
*A61F 2/44* (2006.01)
(Continued)

(52) U.S. Cl.
CPC ........ *A61B 17/025* (2013.01); *A61B 17/0206* (2013.01); *A61B 17/0293* (2013.01);
(Continued)

(58) Field of Classification Search
CPC ..................... A61B 17/025; A61B 2017/0256
See application file for complete search history.

(56) References Cited

U.S. PATENT DOCUMENTS 7,097,648 B1 * 8/2006 Globerman ...... A61B 17/22032
606/99
8,268,000 B2 9/2012 Waugh et al.
(Continued)

FOREIGN PATENT DOCUMENTS

| CN | 102256570 A | 11/2011 |
|---|---|---|
| WO | 2005016131 A2 | 2/2005 |

(Continued)

OTHER PUBLICATIONS

European Patent Office, Application No. 14 851 518.2, Examination Report, Communication pursuant to Article 94(3) EPC, dated Aug. 4, 2020.
(Continued)

*Primary Examiner* — Tessa M Matthews
(74) *Attorney, Agent, or Firm* — Sorell, Lenna & Schmidt, LLP

(57) ABSTRACT

A spinal implant comprises an implant body extending between an anterior surface and a posterior surface, and including a first vertebral engaging surface and a second vertebral engaging surface. The implant body includes an inner surface that defines at least a first cavity and a second cavity. The cavities are oriented to implant fasteners in alignment with an oblique surgical pathway relative to a bilateral axis of a subject body and adjacent an anterior
(Continued)

portion of an intervertebral space of the subject body. Systems and methods are disclosed.

20 Claims, 28 Drawing Sheets

Related U.S. Application Data

(60) Provisional application No. 61/887,803, filed on Oct. 7, 2013.

(51) Int. Cl.
    *A61F 2/46*     (2006.01)
    *A61B 17/70*     (2006.01)
    *A61B 34/20*     (2016.01)
    *A61B 17/80*     (2006.01)
    *A61B 17/88*     (2006.01)
    *A61B 17/00*     (2006.01)
    *A61F 2/30*     (2006.01)
    *A61B 90/00*     (2016.01)

(52) U.S. Cl.
    CPC .......... *A61B 17/70* (2013.01); *A61B 17/7055* (2013.01); *A61B 17/7059* (2013.01); *A61B 17/7074* (2013.01); *A61B 17/7077* (2013.01); *A61B 17/8042* (2013.01); *A61B 17/8872* (2013.01); *A61B 34/20* (2016.02); *A61F 2/4455* (2013.01); *A61F 2/4465* (2013.01); *A61F 2/4611* (2013.01); *A61F 2/4684* (2013.01); *A61B 2017/00004* (2013.01); *A61B 2017/0256* (2013.01); *A61B 2090/3983* (2016.02); *A61F 2/3094* (2013.01); *A61F 2002/30092* (2013.01); *A61F 2002/3092* (2013.01); *A61F 2002/30593* (2013.01); *A61F 2002/30787* (2013.01); *A61F 2002/30836* (2013.01); *A61F 2002/30891* (2013.01); *A61F 2002/30904* (2013.01); *A61F 2310/00017* (2013.01); *A61F 2310/00023* (2013.01); *A61F 2310/00029* (2013.01); *A61F 2310/00293* (2013.01); *A61F 2310/00359* (2013.01); *A61F 2310/00407* (2013.01)

(56) References Cited

U.S. PATENT DOCUMENTS

| | | | |
|---|---|---|---|
| 10,695,044 B2 * | 6/2020 | Miles | A61B 17/025 |
| 10,716,553 B2 * | 7/2020 | Spann | A61B 17/0206 |
| 11,013,616 B2 * | 5/2021 | LaMarca | A61F 2/30771 |
| 2005/0080320 A1 * | 4/2005 | Lee | A61B 17/0206 600/214 |
| 2005/0159650 A1 * | 7/2005 | Raymond | A61B 17/3421 600/201 |
| 2007/0100212 A1 * | 5/2007 | Pimenta | A61B 5/742 600/210 |
| 2008/0249625 A1 | 10/2008 | Waugh et al. | |
| 2009/0036746 A1 | 2/2009 | Blackwell | |
| 2011/0224497 A1 | 9/2011 | Weiman et al. | |
| 2011/0313528 A1 | 12/2011 | Laubert et al. | |
| 2012/0010472 A1 | 1/2012 | Spann | |
| 2012/0010714 A1 | 1/2012 | Moskowitz et al. | |
| 2012/0101580 A1 | 4/2012 | Lechmann et al. | |
| 2012/0245431 A1 * | 9/2012 | Baudouin | A61B 17/0293 600/213 |
| 2012/0303034 A1 | 11/2012 | Woolley | |
| 2013/0190575 A1 * | 7/2013 | Mast | A61B 17/7079 600/215 |
| 2014/0277497 A1 | 9/2014 | Bennett et al. | |
| 2019/0274671 A1 * | 9/2019 | Lauf | A61B 17/025 |

FOREIGN PATENT DOCUMENTS

| | | |
|---|---|---|
| WO | 2008102174 A2 | 8/2008 |
| WO | 2009064644 A1 | 5/2009 |

OTHER PUBLICATIONS

European Patent Office, Office Action, Communication pursuant to Article 94(3) EPC, Application No. 14 852 634.6, dated Aug. 4, 2020.

China National Intellectual Property Administration, Patent/Application No. 201480055408.7, Applicant—Warsaw Orthopedic, Inc., Notice on Reexamination, dated Apr. 29, 2020.

* cited by examiner

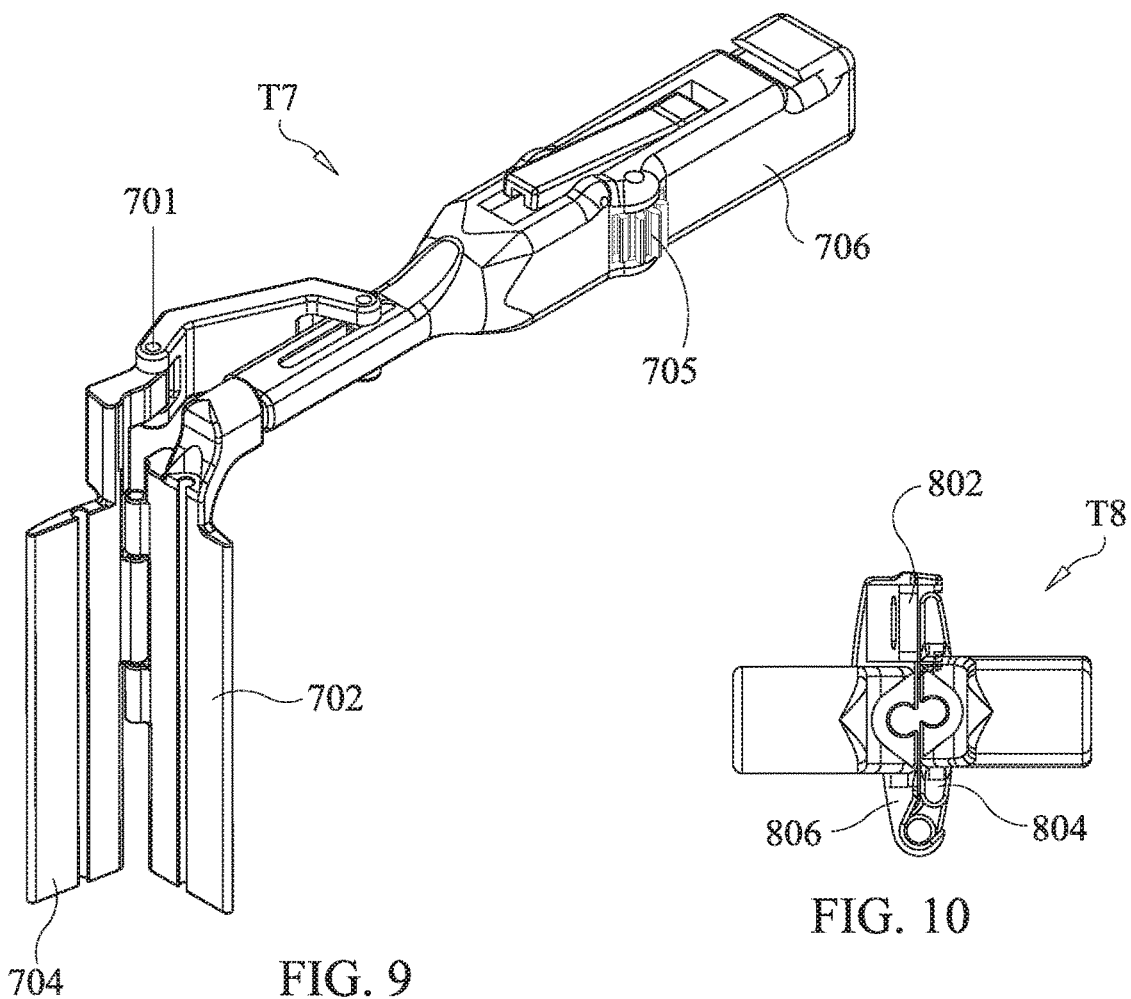
FIG. 9
FIG. 10
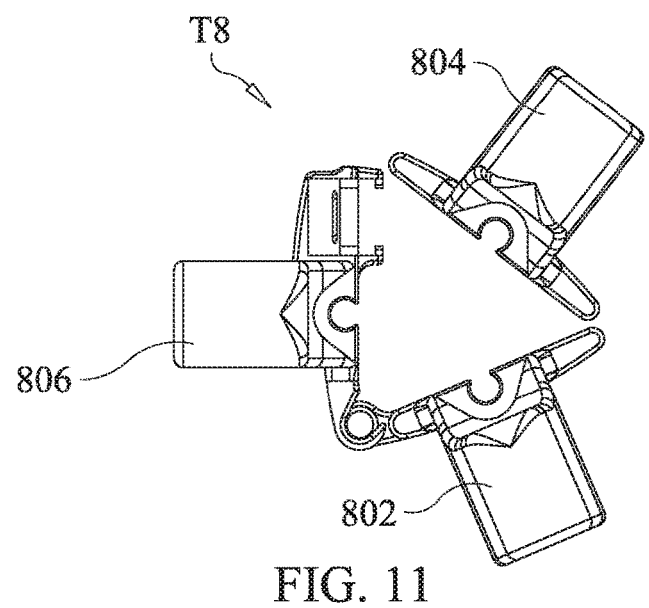
FIG. 11

SPINAL IMPLANT SYSTEM AND METHOD FOR LUMBAR AND LUMBOSACRAL FUSION

CROSS-REFERENCE TO RELATED APPLICATION

This application is a continuation of U.S. patent application Ser. No. 14/494,389, filed Sep. 23, 2014, which claims the benefits of U.S. Provisional Patent Application No. 61/887,803 filed Oct. 7, 2013. These applications are hereby incorporated herein by reference, in their entireties.

TECHNICAL FIELD

The present disclosure generally relates to medical devices for the treatment of musculoskeletal disorders, and more particularly to a spinal implant system and a method for treating a spine, which employ an oblique pathway suitable for accessing disc spaces in the lower lumbar region, for example, an L5-S1 disc space.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, correction, discectomy, laminectomy and implantable prosthetics. As part of these surgical treatments, spinal constructs, such as, for example, bone fasteners, spinal rods and interbody devices can be used to provide stability to a treated region. For example, during surgical treatment, surgical instruments can be used to deliver components of the spinal constructs to the surgical site for fixation with bone to immobilize a joint. This disclosure describes an improvement over these prior art technologies.

SUMMARY

Systems and methods of use for accessing lower lumbar disc spaces via an oblique lateral approach are provided. In some embodiments, a spinal implant comprises an implant body extending between an anterior surface and a posterior surface, and including a first vertebral engaging surface and a second vertebral engaging surface. The implant body includes an inner surface that defines at least a first cavity and a second cavity. The cavities are oriented to implant fasteners in alignment with an oblique surgical pathway relative to a bilateral axis of a subject body and adjacent an anterior portion of an intervertebral space of the subject body.

BRIEF DESCRIPTION OF THE DRAWINGS

The present disclosure will become more readily apparent from the specific description accompanied by the following drawings, in which:

FIG. 9 is a perspective view of components of one embodiment of a system in accordance with the principles of the present disclosure;

FIG. 10 is a top view of components of one embodiment of a system in accordance with the principles of the present disclosure;

FIG. 11 is a top view of components of one embodiment of a system in accordance with the principles of the present disclosure;

DETAILED DESCRIPTION

Figure 1:
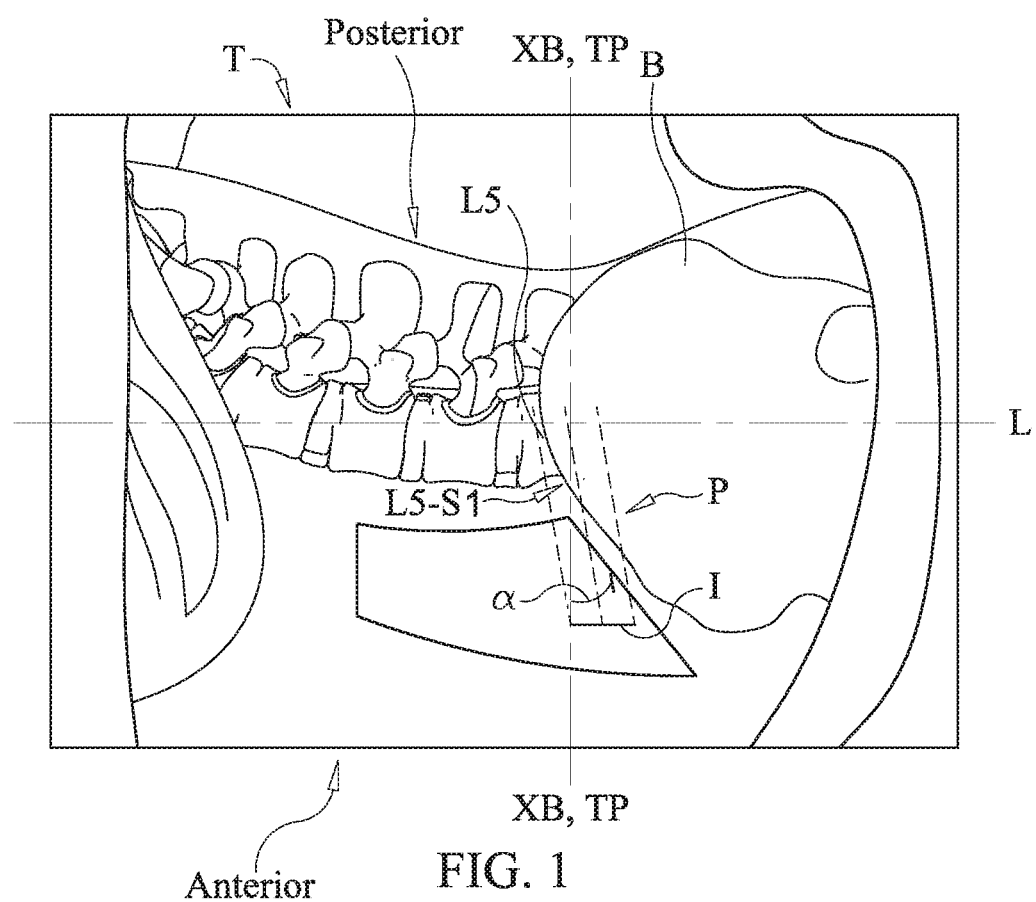
FIG. 1 is a plan view of one embodiment of a system in accordance with the principles of the present disclosure disposed with a subject body.

The exemplary embodiments of the surgical system and related methods of use disclosed are discussed in terms of medical devices for the treatment of musculoskeletal disorders and more particularly, in terms of a surgical system for implant delivery to a surgical site and a method for treating a spine, which employ an oblique surgical pathway. In one embodiment, the systems and methods of the present disclosure are employed with a spinal joint fusion, for example, with a cervical, thoracic, lumbar and/or sacral region of a spine. In one embodiment, an exemplary set of implants and instruments is disclosed for performing a spinal joint fusion in the L5-S1 disc space from an oblique-lateral surgical pathway at a selected oblique angle from the medial plane of the patient. For example, in some exemplary embodiments, the surgical pathway is established at approximately 15 degrees from a medial plane of a patient while the patient is positioned on their side, see FIGS. 1 and 2, generally.

In one embodiment, the surgical system is employed with a method including an oblique lateral interbody fusion (OLIF) procedure in the lower lumbar region between an L5 vertebral body and a sacrum S1 approach using location of a retroperitoneal anatomy and related vascular structures, which may include trans abdominal and retroperitoneal. In one embodiment, the OLIF procedure includes a surgical pathway that is laterally positioned relative to an anterior lumbar interbody fusion (ALIF) retroperitoneal approach. In one embodiment, the procedure avoids dissection of the retroperitoneal space and can be done with a small incision using semi-constrained retractors. In one embodiment, the OLIF procedure avoids the psoas muscle, the iliac crest and both branches of the vasculature in the lower lumbar region. Various embodiments may allow for an oblique lower lumbar procedure that is approached between branched vasculature on an anterior side of a patient in a lower lumbar region, for example, at the L5-S1 vertebral levels.

In one embodiment, the surgical system includes a surgical pathway that is 0-30 degrees off a direct anterior axis. In one embodiment, the surgical pathway is 15 degrees off a direct anterior axis. In one embodiment, the surgical system comprises surgical instruments that include image guided technologies, such as, for example, surgical navigation components employing emitters and sensors, which may be employed to track introduction and/or delivery of the components of the surgical system including the surgical instruments to a surgical site.

In one embodiment, the surgical system includes an interbody implant having threaded locking mechanisms and/or cavities defined therein to orient fasteners oblique relative to a bilateral axis of a subject body. In one embodiment, the surgical system includes an interbody implant having flanges that extend along the OLIF pathway for integrated fixation. In one embodiment, the surgical system includes an interbody implant with a plate. The interbody implant and plate can be inserted together or separately. In one embodiment, the surgical system includes an interbody implant having no or zero profile integrated screws. In one embodiment, the surgical system includes an interbody implant having a posterior cutaway configured to avoid foramen. In one embodiment, the interbody implant can include various shapes, such as, for example, wide, crescent or articulating. In one embodiment, the interbody implant includes a bullet nose.

In one embodiment, the surgical system includes surgical instruments, such as, for example, flexible or semi-constrained retractors utilized to facilitate insertion of one or more components of the surgical system. In one embodiment, a handheld retractor is utilized to facilitate spacing of retractor blades. In one embodiment, the surgical instruments include an all-in-one inserter such that instruments, such as, for example, a drill, tap or awl are guided by the inserter and the inserter is configured to guide screws into tissue.

In one embodiment, the surgical system includes a retractor oriented with a handle on the patient's cephalad side. In one embodiment, the surgical system includes a retractor having three blades. In one embodiment, the blades of the retractor are positioned adjacent to vessels to protect the vessels.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, as used in the specification and including the appended claims, the singular forms "a," "an," and "the"

include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, muscle, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference will now be made in detail to the exemplary embodiments of the present disclosure, which are illustrated in the accompanying figures. Turning to FIGS. 1-28, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites, depending on the particular application and/or preference of a medical practitioner. For example, the components of spinal implant system 10, individually or collectively, can be fabricated from materials such as stainless steel alloys, commercially pure titanium, titanium alloys, Grade 5 titanium, superelastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate such as hydroxyapatite (HA), corraline HA, biphasic calcium phosphate, tricalcium phosphate, or fluorapatite, tri-calcium phosphate (TCP), HA-TCP, calcium sulfate, or other resorbable polymers such as polyaetide, polyglycolide, polytyrosine carbonate, polycaroplaetohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-β), osteoblast cells, growth and differentiation factor (GDF), insulin-like growth factor 1, platelet-derived growth factor, fibroblast growth factor, or any combination thereof.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein. In one embodiment, an interbody cage 12, described herein, may be formed substantially of biocompatible polymer, such as PEEK, and selectively coated with a biocompatible metal, such as titanium, or a bone-growth promoting material, such as HA. In some such embodiments, titanium may be plasma sprayed onto surfaces of interbody cage 12 so as to modify the radiographic signature of cage 12 and/or improve the prospects of bony ongrowth to cage 12 by virtue of the application of a porous or semi-porous coating of titanium.

Figure 2:
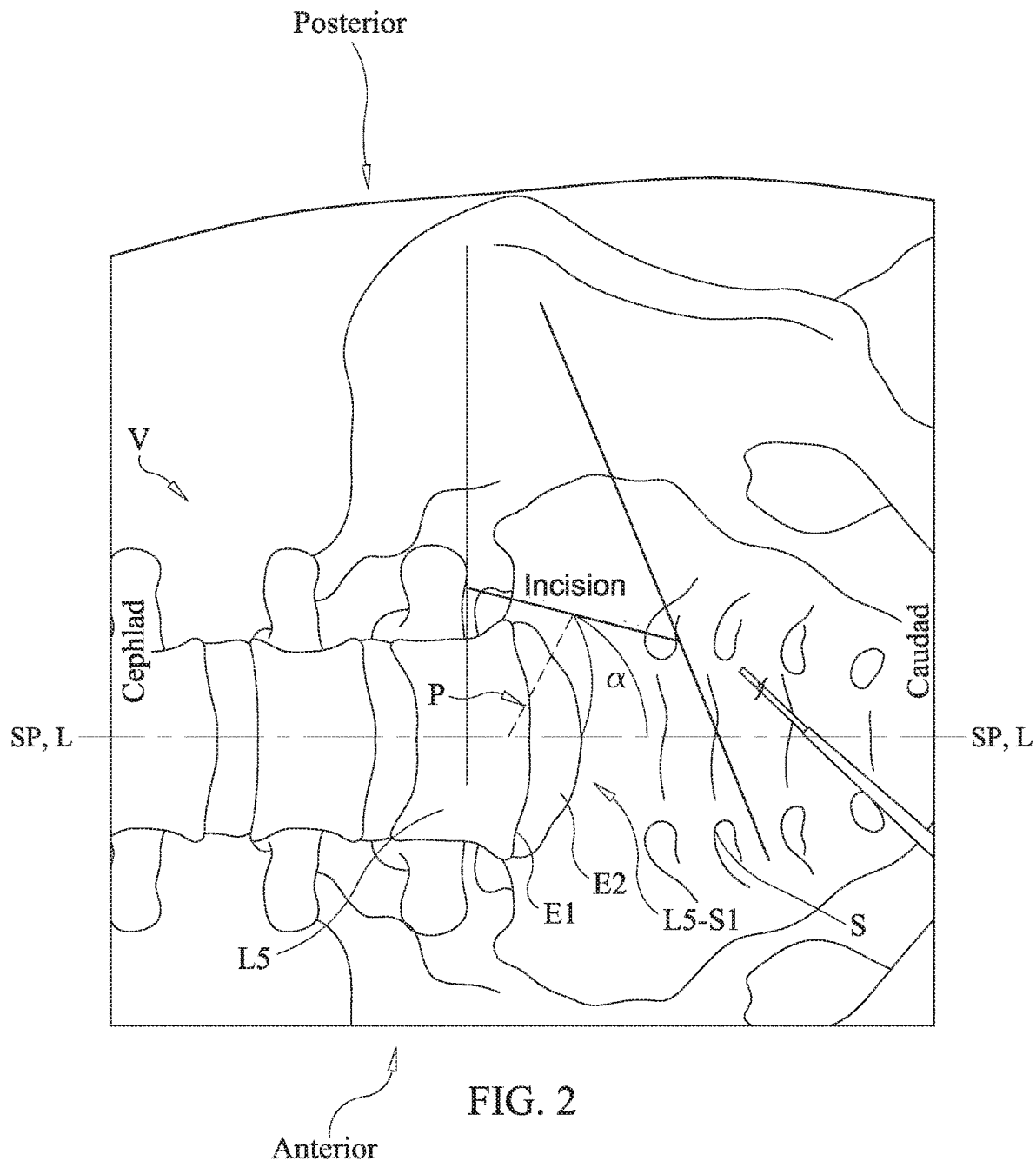
FIG. 2 is a plan view of one embodiment of a system in accordance with the principles of the present disclosure disposed with a subject body.

Spinal implant system 10 may be employed, for example, with minimally invasive procedures, including percutaneous techniques, mini-open surgical techniques and/or open surgical techniques to deliver and introduce instrumentation and/or implants, such as, for example, an interbody implant, at a surgical site within a subject body B of a patient, which includes, for example, a spine having vertebrae V, as shown in FIGS. 1 and 2. In some embodiments, the implant can include spinal constructs, such as, for example, bone fasteners, spinal rods, connectors and/or plates. In other embodiments, various components of the spinal implant system 10 may also be utilized in "open" or traditional spinal surgical techniques. In many of the embodiments described herein, the patient is positioned on their side for the surgical procedure and the surgeon may stand on an anterior side of the patient so as to be capable of standing directly above the oblique-anterior and/or oblique lateral surgical pathway established.

Figure 14:
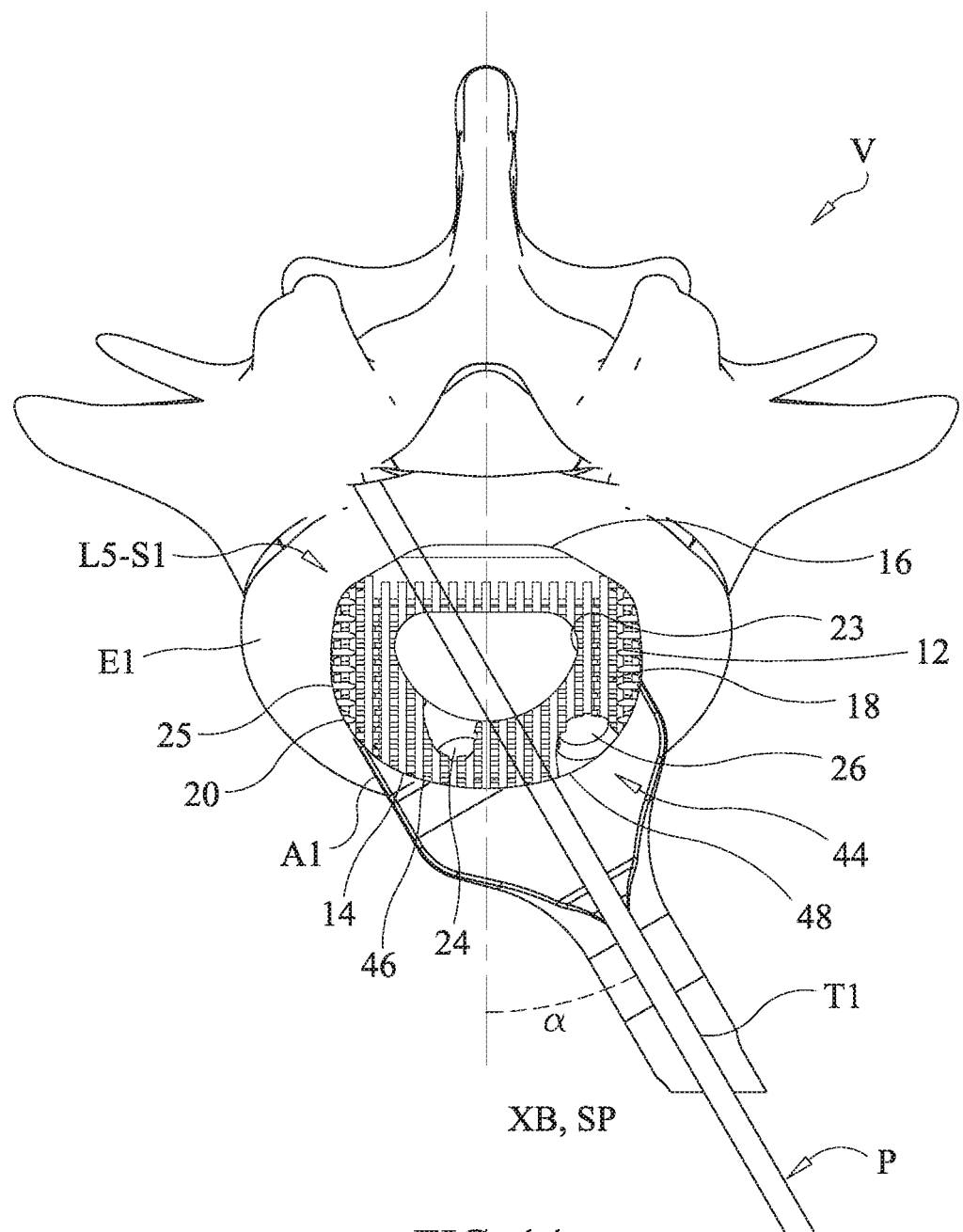
FIG. 14 is an axial view of components of one embodiment of a system in accordance with the principles of the present disclosure disposed with vertebrae.
Figure 15:
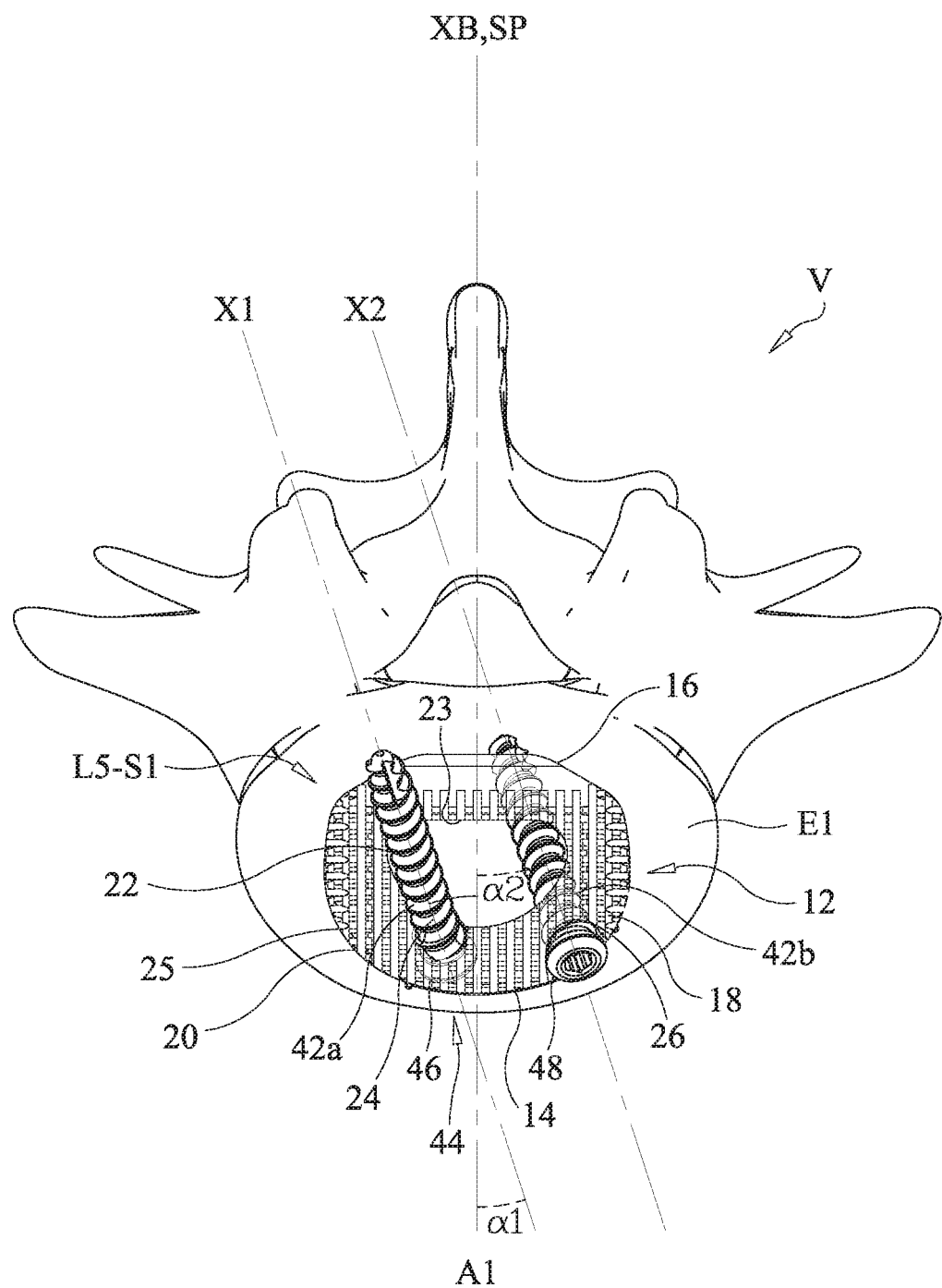
FIG. 15 is an axial view of components of the system and the vertebrae shown in FIG. 14.

Spinal implant system 10 includes an implant body, such as, for example, interbody cage 12, as shown in FIGS. 14 and 15. Cage 12 extends between an anterior surface 14 and a posterior surface 16. Anterior surface 14 is configured to face an anterior side of body B and be disposed adjacent an anterior portion of vertebrae, such as, for example, an anterior portion A1 of an L5-S1 intervertebral space of vertebrae V. Posterior surface 16 is configured to face a posterior side of body B and be disposed adjacent a posterior portion of vertebrae, such as, for example, a posterior portion of the L5-S1 intervertebral space.

Cage 12 includes a first vertebral engaging surface 18 and a second vertebral engaging surface 20. Surface 18 is substantially planar and configured to engage endplate tissue of a vertebral body, such as, for example, an endplate E1 of an L5 vertebral body, as shown in FIG. 2. Surface 20 is configured to engage endplate tissue of a vertebral body, such as, for example, an endplate E2 of a sacrum S1. In some embodiments, surfaces 18, 20 may be rough, textured, porous, semi-porous, dimpled, knurled, toothed, grooved and/or polished such that it facilitates engagement with tissue. In some embodiments, the vertebral tissue may include intervertebral tissue, endplate surfaces and/or cortical bone.

Cage 12 may be provided with a substantially cylindrical cross section configuration and includes an inner surface 22 that defines an opening 23 configured to receive an agent, which may include bone graft (not shown) and/or other materials, as described herein, for employment in a fixation or fusion treatment. In some embodiments, the cross-sectional geometry of cage 12 may have various configurations, such as, for example, round, oval, oblong, triangular, polygonal having planar or arcuate side portions, irregular, uniform, non-uniform, consistent, variable, horseshoe shape, U-shape or kidney bean shape. In some embodiments, cage 12 includes an outer surface 25 that is smooth or even. In some embodiments, outer surface 25 may be rough, textured, porous, semi-porous, dimpled and/or polished.

Inner surface 22 includes internally threaded portions and/or non-threaded portions that define cavities, such as, for example, a screw hole 24 and a screw hole 26, as shown in FIG. 14. Screw hole 24 extends along the body of cage 12 in a transverse configuration relative to the surfaces of cage 12, described herein, for fixation with tissue. Screw hole 24 is oriented with the body of cage 12 in substantial alignment with an oblique surgical pathway P formed in body B, as described herein. Surgical pathway P is oriented oblique relative to a bilateral axis XB of body B. In some embodiments, surgical pathway P is disposed at an oblique angle α relative to axis XB. In some embodiments, angle α is in a range of approximately 0-60 degrees. In some embodiments, substantial alignment of all or only a portion of screw hole 24 with all or only a portion of surgical pathway P includes co-axial, spaced apart, offset, angularly offset and/or parallel alignment.

Screw hole 24 defines an axis X1 oriented oblique relative to axis XB such that screw hole 24 implants a fastener, as described herein, oblique relative to axis XB and adjacent portion A1. Axis XB lies in a transverse plane TP defined by body B corresponding to the L5-S1 intervertebral space, as shown in FIG. 1. Axis XB also lies in a sagittal plane SP, as shown in FIG. 2, defined by body B such that planes TP, SP intersect adjacent axis XB. Vertebrae V defines a substantially longitudinal axis L, which lies in plane SP.

Axis X1 is disposed in substantial alignment with surgical pathway P and at an oblique angle α1 relative to axis XB. In some embodiments, angle α1 is in a range of approximately 0-60 degrees. In one embodiment, angle α1 is approximately 15 degrees relative to axis XB and substantially aligned with surgical pathway P such that screw hole 24 is configured to receive a fastener via surgical pathway P. In some embodiments, screw hole 24 is also disposed at an angular orientation relative to plane TP and/or axis XB such that a fastener is delivered to a surgical site including the L5-S1 intervertebral space via surgical pathway P and oriented to penetrate endplate tissue of a vertebral body, such as, for example, an endplate E2 of a sacrum S1. In some embodiments, screw hole 24 and/or the body of cage 12 may be disposed at an angular orientation relative to plane TP and/or axis XB such that a fastener is oriented to penetrate endplate tissue of a vertebral body.

Outer surface 25 includes an oblique surface 44 that defines an opening 46 disposed in communication and substantial alignment with screw hole 24. Oblique surface 44 is oriented with cage 12 and in substantial alignment with surgical pathway P. Opening 46 is configured to guide a fastener into screw hole 24 relative to axis XB and in substantial alignment with surgical pathway P. In some embodiments, oblique surface 44 is configured for mating engagement with a surgical instrument, such as, for example, an inserter T1, as shown in FIG. 14, which delivers cage 12 adjacent a surgical site via surgical pathway P, as described herein. In some embodiments, system 10 may comprise various surgical instruments, such as, for example, drivers, extenders, reducers, spreaders, distractors, blades, clamps, forceps, elevators and drills, which may be alternately sized and dimensioned, and arranged as a kit. In some embodiments, system 10 may comprise various surgical instruments, such as, for example, drivers, extenders, reducers, spreaders, distractors, blades, clamps, forceps, elevators and drills, which may be alternately sized and dimensioned, and arranged as a kit. In some embodiments, system 10 may comprise the use of microsurgical and image guided technologies, such as, for example, surgical navigation components employing emitters and sensors, which may be employed to track introduction and/or delivery of the components of system 10 including the surgical instruments to a surgical site. See, for example, the surgical navigation components and their use as described in U.S. Pat. Nos. 6,021,343, 6,725,080, 6,796,988, the entire contents of each of these references being incorporated by reference herein. An exemplary all-in-one inserter and guide instrument for cage 12 is shown, for example, in FIGS. 19 and 20 described herein.

Screw hole 26 extends along the body of cage 12 in a transverse configuration relative to the surfaces of cage 12, described herein, for fixation with tissue. Screw hole 26 is oriented with the body of cage 12 in substantial alignment with surgical pathway P. In some embodiments, substantial alignment of all or only a portion of screw hole 26 with all or only a portion of surgical pathway P includes co-axial, spaced apart, offset, angularly offset and/or parallel alignment.

Screw hole 26 defines an axis X2 oriented oblique relative to axis XB such that screw hole 26 implants a fastener, as described herein, oblique relative to axis XB and adjacent portion A1. Axis X2 is disposed in substantial alignment with surgical pathway P and at an oblique angle α2 relative to axis XB. In some embodiments, angle α2 is in a range of approximately 0-60 degrees. In one embodiment, angle α2 is approximately 15 degrees relative to axis XB and substantially aligned with surgical pathway P such that screw hole 26 is configured to receive a fastener via surgical pathway P. In some embodiments, screw hole 26 is also disposed at an angular orientation relative to plane TP and/or axis XB such that a fastener is delivered to a surgical site including the L5-S1 intervertebral space via surgical pathway P and oriented to penetrate endplate tissue of a vertebral body, such as, for example, an L5 vertebral body. In some embodiments, screw hole 26 and/or the body of cage 12 may be disposed at an angular orientation relative to plane TP and/or axis XB such that a fastener is oriented to penetrate endplate tissue of a vertebral body. In some embodiments, angle α, α1 and/or α2 may be equal, substantially equivalent and/or different. In some embodiments, surgical pathway P, axis X1 and/or axis X2 may be co-axial, spaced apart, offset, angularly offset and/or parallel alignment.

Oblique surface 44 defines an opening 48 disposed in communication and substantial alignment with screw hole 26. Opening 48 is configured to guide a fastener into screw hole 26 relative to axis XB and in substantial alignment with surgical pathway P. In some embodiments, the cross section configurations of screw holes 24, 26 may be, such as, for example, oval, oblong, triangular, square, polygonal, irregular, uniform, non-uniform, offset, staggered, undulating, arcuate, variable and/or tapered. In some embodiments, surface 22 may have alternate surface configurations to define cavities, similar to screw holes 24, 26, for receiving fasteners, such as, for example, nails or pins.

Spinal implant system 10 includes one or more fasteners 42, as shown in FIG. 15, for attaching cage 12 with tissue, as described herein. In some embodiments, fasteners 42 may be engaged with tissue in various orientations, such as, for example, series, parallel, offset, staggered and/or alternate vertebral levels. In some embodiments, one or more of fasteners 42 may comprise multi-axial screws, sagittal angulation screws, pedicle screws, mono-axial screws, uni-planar screws, facet screws, fixed screws, tissue penetrating screws, conventional screws, expanding screws, wedges, anchors, buttons, dips, snaps, friction fittings, compressive fittings, expanding rivets, staples, nails, adhesives, posts, fixation plates and/or posts.

Each fastener 42 comprises a first portion, such as, for example, a head and a second portion, such as, for example, an elongated shaft configured for penetrating tissue. The head includes an engagement portion configured for engagement with a surgical instrument. The shaft has a cylindrical cross section configuration and includes an outer surface having an external thread form. In some embodiments, the external thread form may include a single thread turn or a plurality of discrete threads. In some embodiments, other engaging structures may be located on the shaft, such as, for example, nail configuration, barbs, expanding elements, raised elements and/or spikes to facilitate engagement of the shaft with tissue, such as, for example, vertebrae.

In some embodiments, all or only a portion of the shaft may have alternate cross section configurations, such as, for example, oval, oblong, triangular, square, polygonal, irregular, uniform, non-uniform, offset, staggered, undulating, arcuate, variable and/or tapered. In some embodiments, the outer surface of the shaft may include one or a plurality of openings. In some embodiments, all or only a portion of the outer surface of the shaft may have alternate surface configurations, such as, for example, smooth and/or surface configurations to enhance fixation with tissue, such as, for example, rough, arcuate, undulating, porous, semi-porous, dimpled, polished and/or textured. In some embodiments, all or only a portion of the shaft may be cannulated.

In assembly, operation and use, as shown in FIGS. 1-15, spinal implant system 10, similar to the systems described herein, is employed with a surgical procedure for treatment of a spinal disorder, such as those described herein, affecting a section of a spine of a patient. System 10 may also be employed with other surgical procedures. To treat the affected section of vertebrae V of a subject body B of a patient, body B is disposed in a side orientation, as shown in FIGS. 1 and 2, relative to a surgical fixed surface, such as, for example, surgical table T configured for supporting body B. Body B is placed on a side, left side up. In some embodiments, this results in the vena cava being oriented on the right side of centerline. Body B is oriented such that the procedure can be performed obliquely in front of the iliac crest to provide direct access to L5-S1 intervertebral space along surgical pathway P, described herein, while avoiding selected muscular and abdominal anatomical structures. In some embodiments, placement of body B on its side facilitates access to surgical pathway P that is disposed at oblique angle α relative to axis XB.

Figure 3:
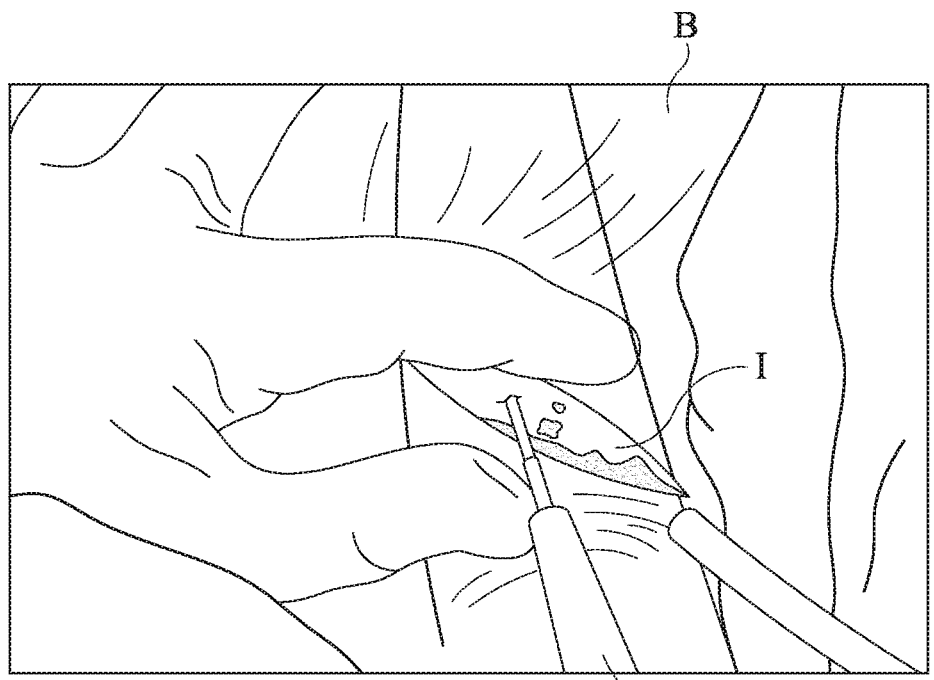
FIG. 3 is a plan view of components of one embodiment of a system in accordance with the principles of the present disclosure disposed with a subject body.

A marking, as shown in FIG. 2, is drawn from the anterior of body B to the posterior of body B to identify the slope and lordosis of the L5-S1 intervertebral space and the line is continued along the same trajectory as the slope onto the abdomen for accessing surgical pathway P. The amount of slope visually indicates the most caudal, toward the coccyx, aspect of the incision to enter the lordosis of the L5-S1 intervertebral space with respect to the cephalad, towards the head. A second line is drawn from the center of the disc and projecting perpendicular to the floor onto the abdomen. This line represents the actual level of the disc in the abdomen. An incision I, as shown in FIGS. 2 and 3, is made with a surgical instrument, such as, for example, a scalpel T2, for substantial alignment and communication to create surgical pathway P from posterio-rostral to antero-caudal medial approximately 1-2 finger breaths from the ASIS and pelvis, between the two lines. In some embodiments, the incision can extend to higher levels of the spine and distally to the symphisis pubis. In one embodiment, a separate L5-S1 incision is utilized at a site lower and more anterior than the L4-L5.

In some embodiments, the external oblique muscle or the aponeurosis and fascia are encountered upon entry into incision I. In some embodiments, the retroperitoneal dissection and exposure is accomplished by utilizing a blunt finger so as to facilitate a wider exposure for the retractors. In some embodiments, the ureter is exposed and dissection of a wide rostral to caudal development of the retroperitoneal plane is utilized to protect the ureter, thereby maintaining its attachment to the posterior peritoneum while mobilizing anteriorly.

In some embodiments, surgical pathway P is created with the progression of the two finger dissection down the pelvis and across the psoas continues anteriorly from the pelvis to locate the iliac artery pulse. In some embodiments, the finger dissection is continued past the pulsating iliac artery medial to the artery on the sacral promontory and the L5-S1 intervertebral space. In some embodiments, lighted retractors are placed sequentially down onto the anterior spine and the adventitial layers that are on the anterior disc and sacrum are encountered.

In some embodiments, the oblique approach creating surgical pathway P accesses the L5-S1 intervertebral space below the bifurcation, as such, the iliolumbar vein is not ligated since posterior retraction of the left common iliac vein and artery laterally does not cause stretch and potential avulsion. In some embodiments, the L4/L5 is anteriorly retracted and an implant can be inserted obliquely thereby avoiding mobilization of the vessels.

Figure 4:
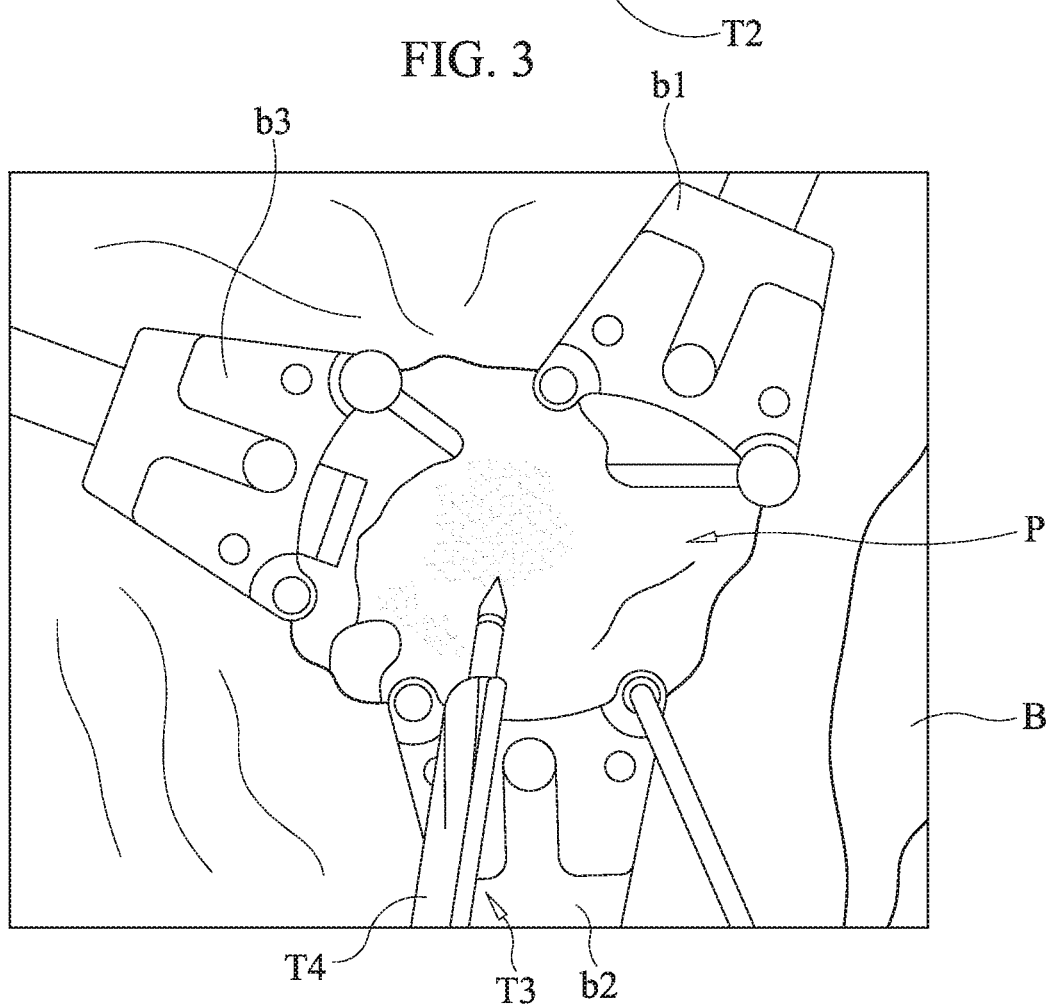
FIG. 4 is a plan view of components of one embodiment of a system in accordance with the principles of the present disclosure disposed with a subject body.

In some embodiments, as shown in FIG. 4, a surgical instrument, such as, for example, a retractor T3 is disposed with incision I and in communication with surgical pathway P for spacing tissue. Retractor blades b1, b2, b3 are inserted sequentially around the L5-S1 intervertebral space to protect vessels. A lateral or posterior blade b1 is placed under the iliac vein to release the adventitial layer to secure protection and lateralization of the left iliac vein and artery. Blade b1 may be provided with an elevation that permits direct visualization of a smooth pin (not shown) placement. In some embodiments, the pin is blunt nosed to push away vascular structures and the threads are smooth to prevent wrapping up soft tissue. In some embodiments, a screw is malleted or screwed in and secures on one side of blade b1. As shown generally in FIGS. 4A and 4B, blades b1, b2 and b3 may be provided with channels 411, 412, 413a, 413b, through which securing pins may be placed to secure the blades relative to the bony anatomy of the surgical site.

An anterior blade b2 is disposed with incision I and about the L5-S1 intervertebral space. In one embodiment, a final cephalad blade b3 is disposed with the L5-S1 intervertebral space to protect the vascular bifurcation. In one embodiment, an additional blade may be placed caudally to create a completely closed surgical pathway. In some embodiments, an annulotomy and/or discectomy is performed with a surgical instrument T4 with x-ray confirmation of the starting point that is central on the L5-S1 intervertebral space. In some embodiments, system 10 includes a semi-constrained retractor that facilitates minimal tissue pressures on surrounding abdominal structures and provides flexibility such that its blades rotate on a fixed pin allowing greater degrees of freedom of movement and working angles for a practitioner.

Figure 4A:
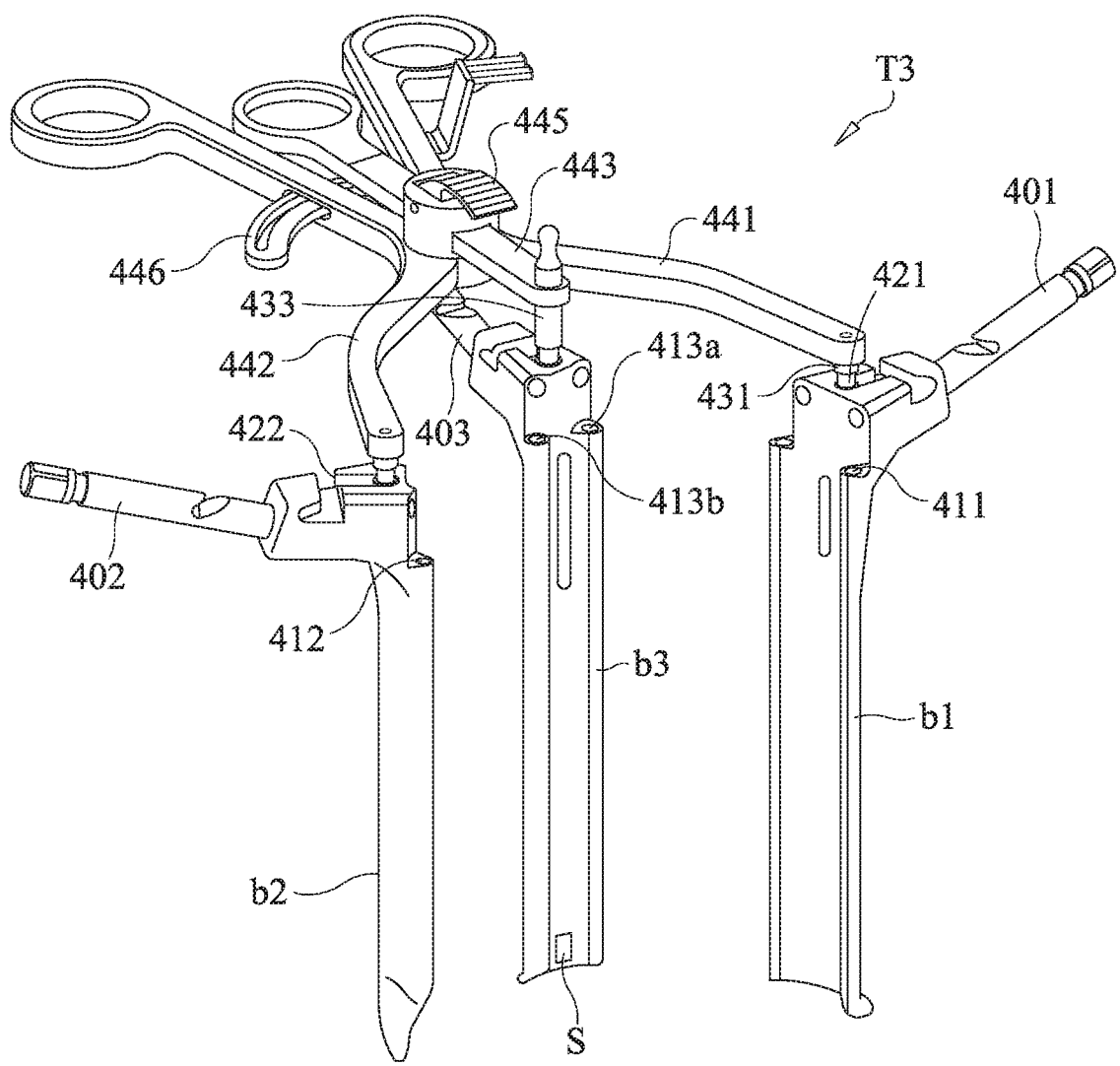
FIG. 4A is a perspective view of components of one embodiment of a system in accordance with the principles of the present disclosure.
Figure 4B:
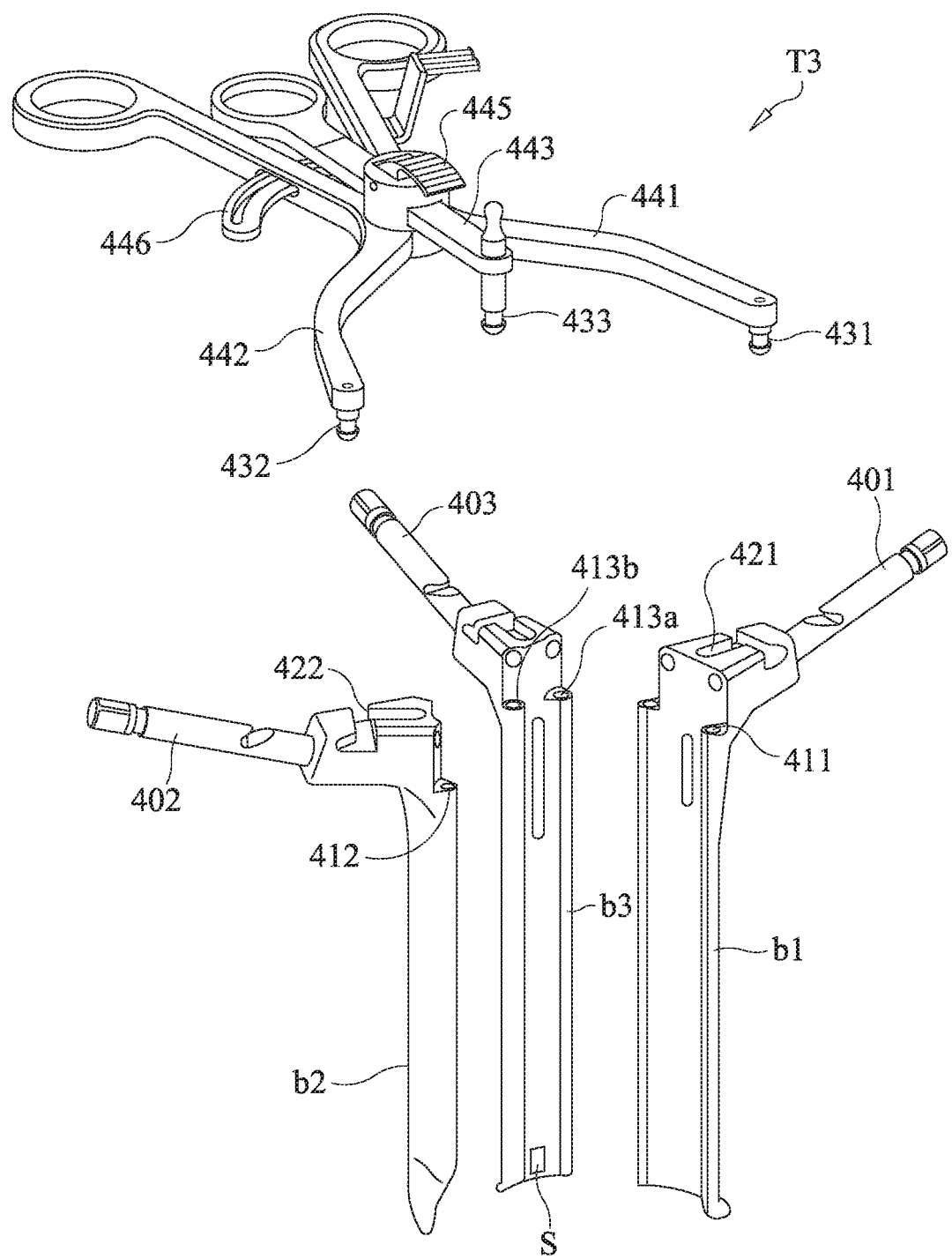
FIG. 4B is a perspective view of the components shown in FIG. 4A with parts separated.

In some embodiments, as shown in FIGS. 4A and 4B, a semi-constrained retractor system with separable blades may be used to sequentially insert blades b1, b2, b3. Alternatively, the blades b1, b2, b3 may be removably secured to a handheld retractor T3 via a system of pins 431, 432, 433 on each blade that may be removably engaged with complementary recesses 421, 422, 432 defined in the proximal ends of blades b1, b2, b3. The blades b1, b2, b3 may also be fitted with attachment rods 401, 402, 403 configured to be capable of securing to a frame, handle, or other attachment mechanism so as to be individually or simultaneously manipulated when either attached or not attached to the handheld retractor T3. The retractor T3 may be provided with three arms 441, 442, 443 for manipulating the blades b1, b2, b3 when they are attached thereto. Arms 441, 442 may be capable of spreading blades b1, b2 away from one another along a generally anterior-posterior direction. Furthermore a third arm 443 may be capable of translating to move the blade b3 in the cephalad direction, see FIG. 12, for example, showing an exemplary position of blade b3. Arms 441, 442 may be engaged in a ratcheting mechanism 446 such that handheld manipulation of the retractor T3 by a surgeon may hold the blades b1, b2 apart at a selected distance defined in part by the ratcheting mechanism 446. Arm 443 may have a separate ratcheting slide 445, allowing a surgeon to independently manipulate and hold blade b3 at a selected distance in the from the blades b1, b2.

Figure 12:
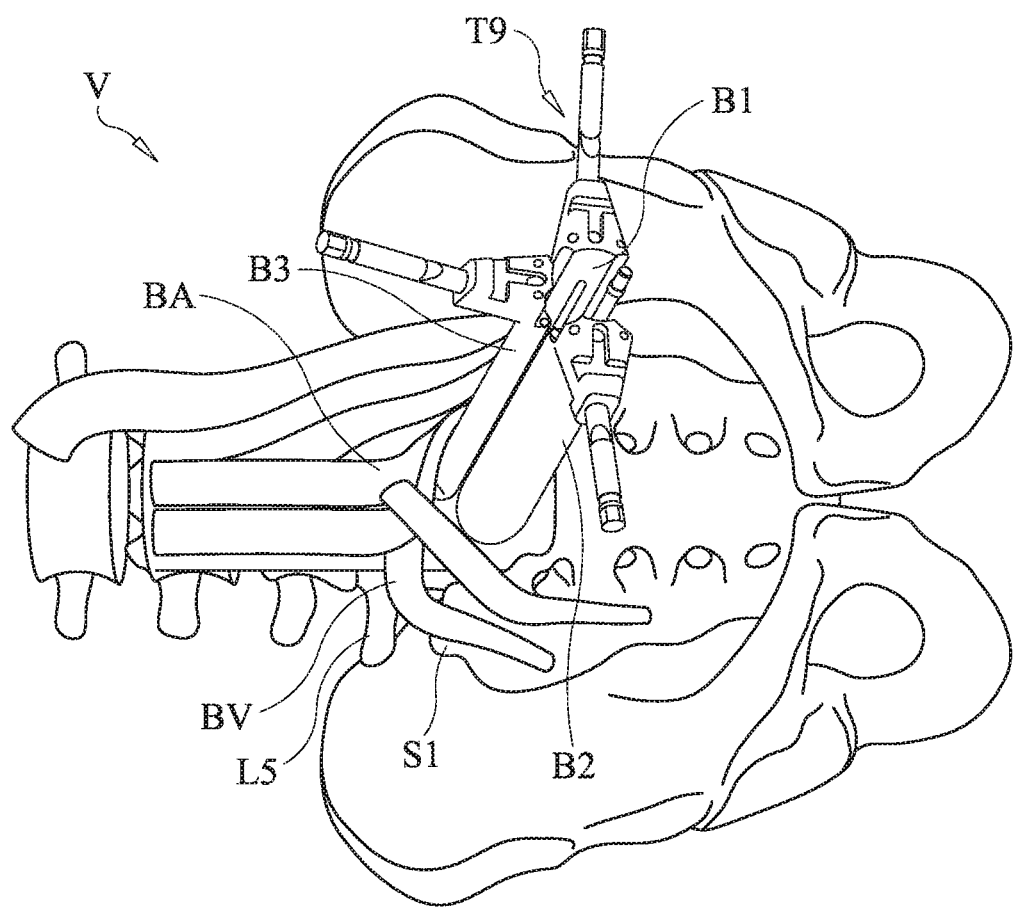
FIG. 12 is a perspective view of components of one embodiment of a system in accordance with the principles of the present disclosure disposed with a subject body.

In one embodiment, a cephalad blade b3 is oriented toward the vasculature bifurcation near L5-S1 to secure protection of the vessels at the bifurcations BA, BV (FIG. 12). Anterior blade b2 and posterior blades b1 and b2 are oriented about the L5-S1 intervertebral space to protect the remaining vessels caudal to the bifurcations BA, BV. Blades b1, b2, b3 may define channels 411, 412, 413a, 413b, through which securing pins may be placed to secure the blades relative to the bony anatomy of the surgical site. Blade b3 may have an elevation and/or distal curvature that permits direct visualization of a smooth pin placement. In some embodiments, securing pin is blunt nosed to push away vascular structures and the threads are smooth to prevent wrapping up soft tissue. In some embodiments, a screw is malleted or screwed in and secures on one side of blade b1, for example in channel 411. In some embodiments, blade b3 may be equipped with a curved distal end to sweep and/or elevate vascular structures, such as the bifurcations BA, BV, shown in FIG. 12, away from the surgical site. In one embodiment, anterior blade b3 may be provided with sensors S for detecting and/or measuring blood flow near the surgical site to ensure that the most relevant and sensitive vascular structures near the surgical site are safely separated from the oblique-lateral and/or oblique spinal surgical pathway. Sensors S may include, such as, for example, piezoelectric elements; ultrasound emitters and/or receivers, flowmeters; oximeters; pulse meters; and/or other available medical devices useful for identifying and/or localizing blood vessels. In some embodiments, anterior blade b3 may be clear, translucent, or a substantially clear material, such as, for example, a clear polymer, to allow a surgeon to directly visualize structures on the anterior side of anterior blade b3 during the surgical procedure.

Figure 5:
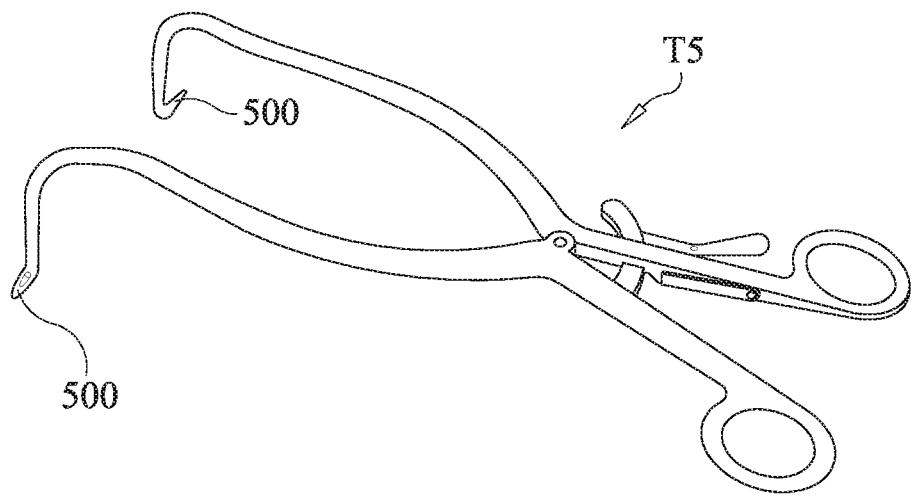
FIG. 5 is a perspective view of a component of one embodiment of a system in accordance with the principles of the present disclosure.
Figure 6:
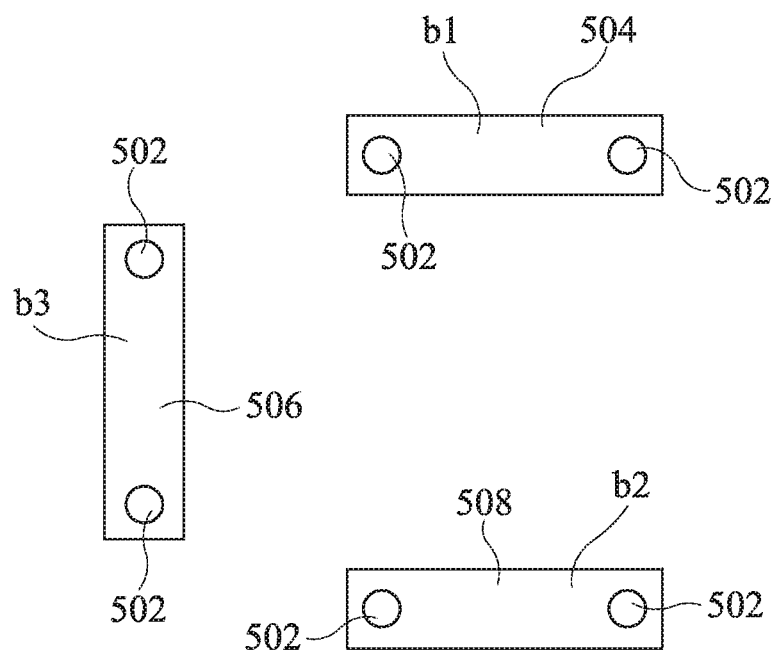
FIG. 6 is a plan view of components of one embodiment of a system in accordance with the principles of the present disclosure.

In one embodiment, as shown in FIGS. 5 and 6, system 10, similar to the systems and methods described herein, includes a flexible or semi-constrained retractor, which is not attached to a rigid frame and facilitates adjustment and allows for freedom of movement when manipulating implants, as described herein. A surgical instrument, such as, for example, a retractor T5 is provided with downward oriented tips 500 configured for engagement with corresponding pin holes 502 defined in individual retractor blades 504, 506, 508. As shown in FIG. 6, the positioning of blades 504, 506, 508 may correspond to the relative positioning of blades b1, b2, b3 shown generally in FIG. 12. Retractor T5 is configured to facilitate spacing of adjacent or opposing blades 504, 506, 508. In one embodiment, pin holes 502 in retractor blades 504, 506, 508 are configured to receive other surgical instruments, such as, for example, lighting tubes, pins for securing at least one of blades 504, 506, 508 to a bony structure, the downward facing tips attached to a second retractor, or rubber bands.

Figure 6A:
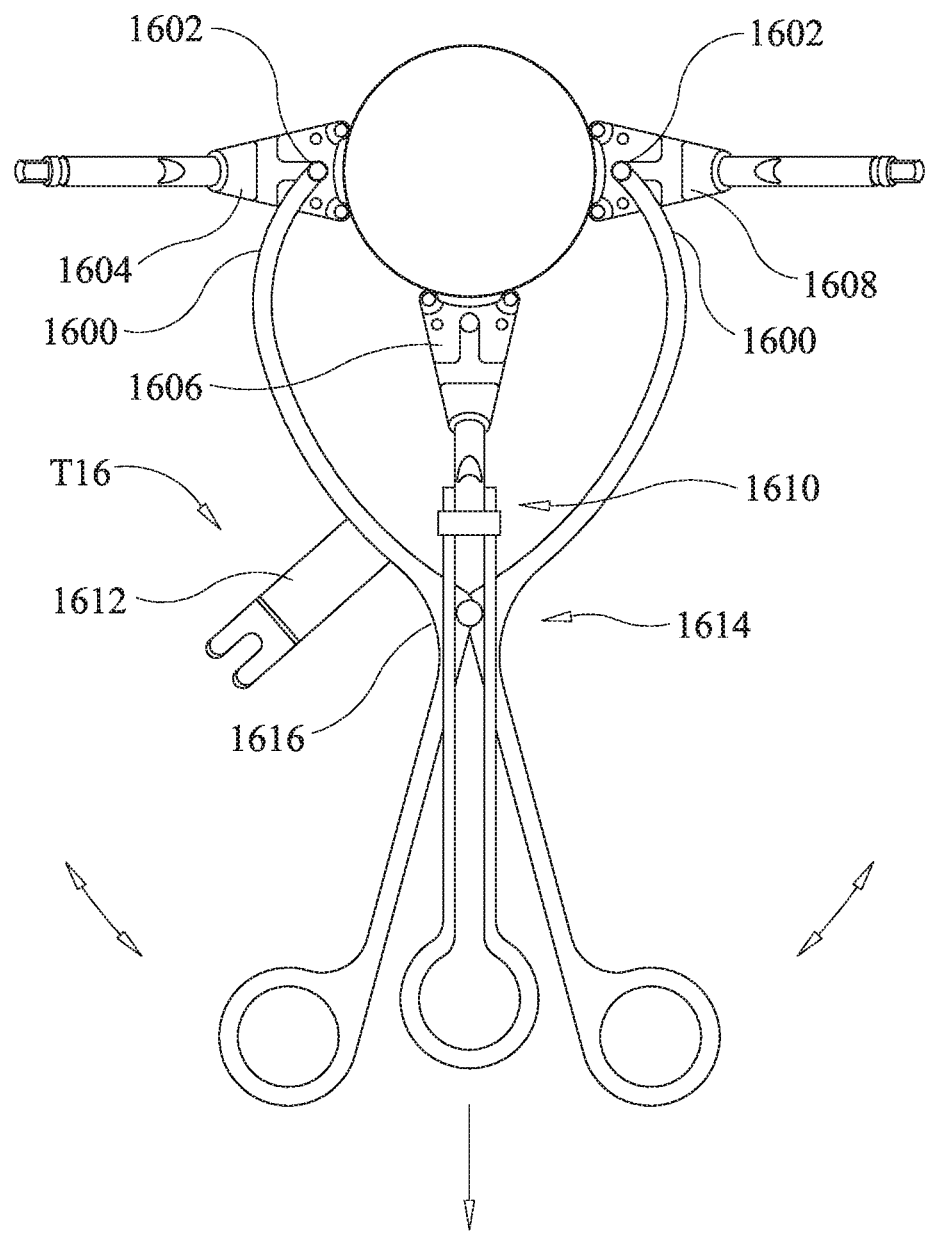
FIG. 6A is a plan view of components of one embodiment of a system in accordance with the principles of the present disclosure.

In one embodiment, as shown in FIG. 6A, similar to the systems and methods described herein with respect to FIGS. 4A and 4B, includes a flexible or semi-constrained retractor T16 having spacing for a three finger manipulation. Retractor T16 includes a flexible arm attachment 1612 for connection to a fixed point, such as a pin or frame rigidly or adjustable attached to an operating table. Retractor T16 includes tips 1600 that are configured for engagement with central pivot holes 1602 defined in individual retractor blades 1604 and 1608. Retractor T16 includes a shoulder 1610 mounted with a retractor blade 1606. Shoulder 1610 includes a ratchet 1614 for adjustment of blade 1606 position and one way locking. Shoulder 1610 includes a release 1616 that disengages ratchet 1614 to facilitate bi-directional movement of blade 1606.

Figures 7, 8:
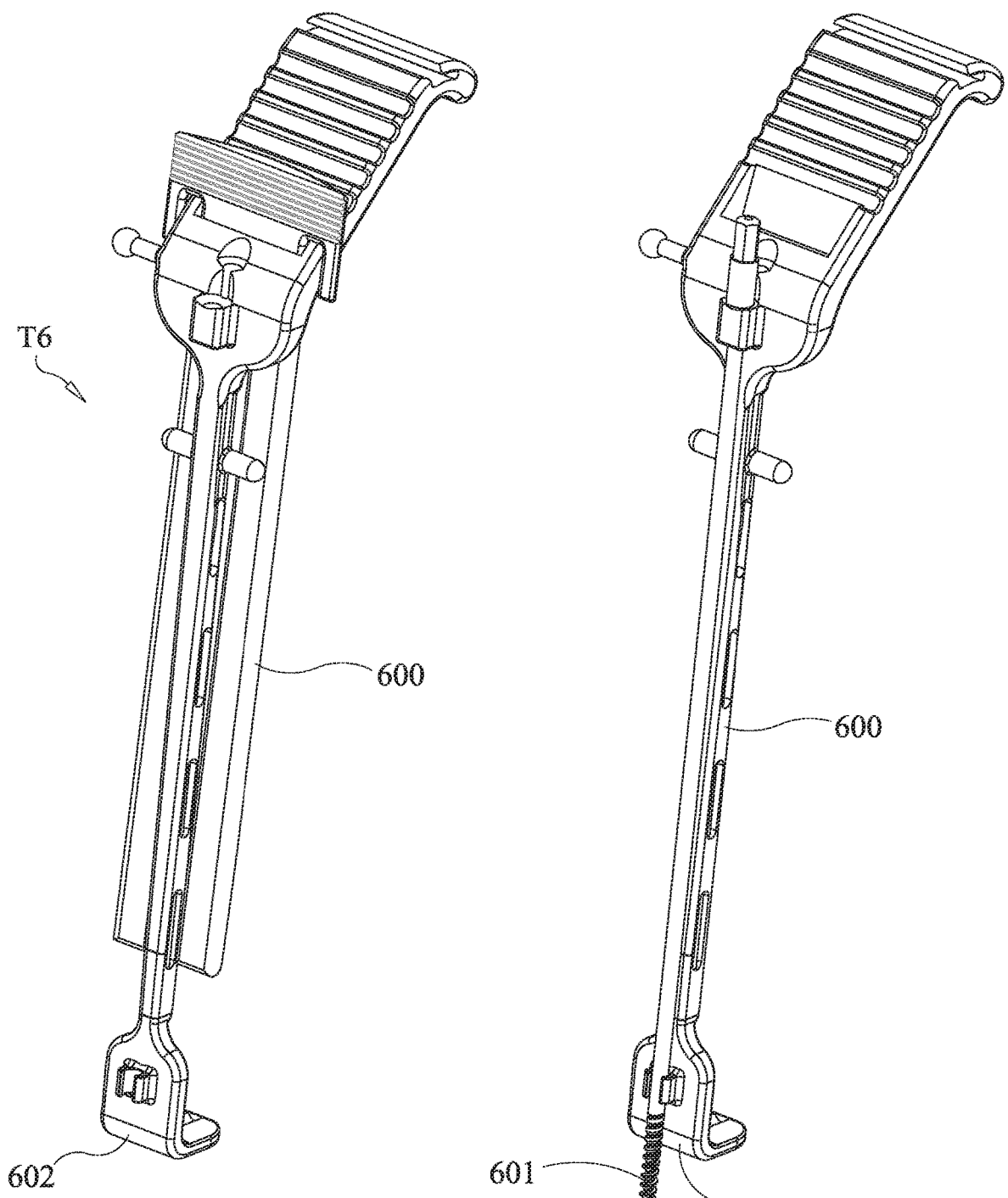
FIG. 7 is a perspective view of a component of one embodiment of a system in accordance with the principles of the present disclosure.
FIG. 8 is a perspective view of components of one embodiment of a system in accordance with the principles of the present disclosure.

In one embodiment, as shown in FIGS. 7 and 8, a surgical instrument, such as, for example, a specialized retractor blade T6 is shown that facilitates movement of vasculature with a securing pin 601, as shown in FIG. 8, or without a securing pin, as shown in FIG. 7. Retractor T6 includes a blade 600 having a curved distal end 602 configured to safely move or hold vasculature away from a surgical site while a surgeon is working in the operative corridor. For example, the specialized blade T6 may be used in lieu of or with the blades b1, b2, b3, for example, being selectively attached to a handheld retractor T3 such as that described herein with respect to FIGS. 4A and 4B. In one embodiment, as shown in FIG. 9, a surgical instrument is provided, such as, for example, a retractor T7 provided with two blades 702, 704 and a ratchet mechanism 706 for incremental and controlled movement of blades 702, 704 at a surgical site. The retractor T7 may be a hand-held retractor for maintaining a surgical corridor by actuating a thumbwheel 705 that actuates a mechanism for spreading the blades 702, 704 apart along a single axis 701.

In one embodiment, as shown in FIGS. 10 and 11, system 10, similar to the systems and methods described herein, includes a surgical instrument, such as, for example, a retractor T8, which includes blades 802, 804, 806 that are configured to form a closed operative corridor. Blade 802 is disposed adjacent to the vessels, as described herein, and protects the surrounding vessels. In one embodiment, blade 802 may include a curved distal lip, similar to that shown as element 602 in FIG. 7, on a distal tip configured to protect vessels.

Figure 12A:
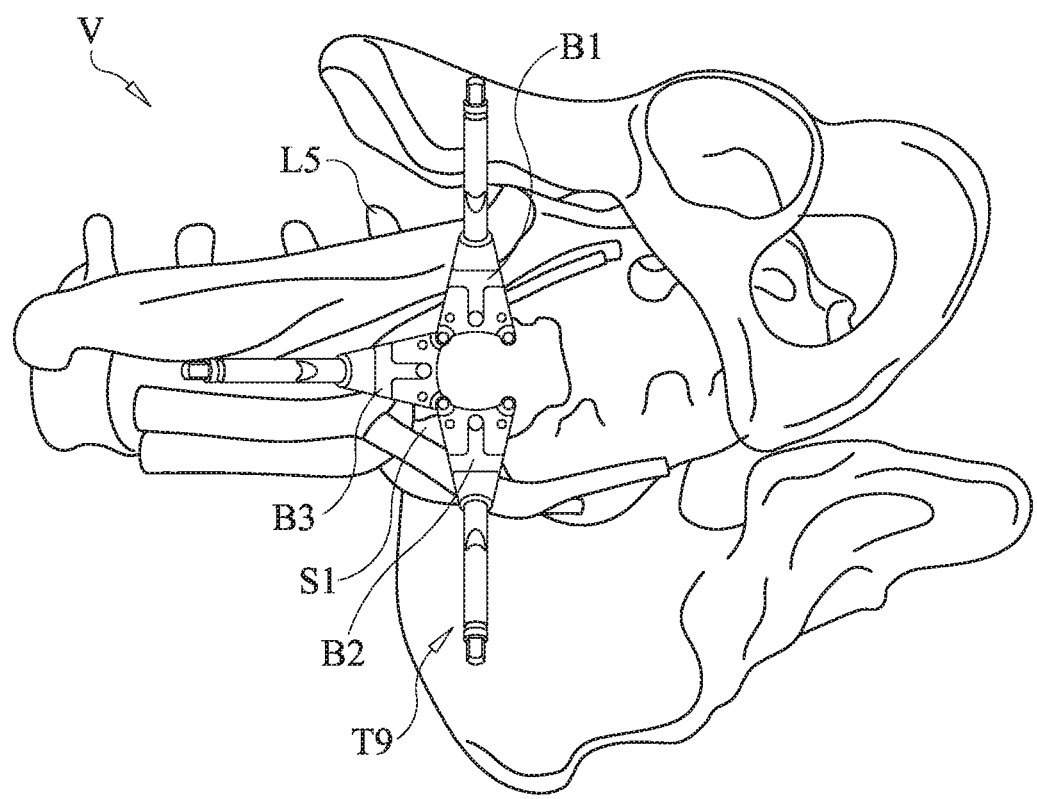
FIG. 12A is a perspective view of the components and subject body shown in FIG. 12.
Figure 13:
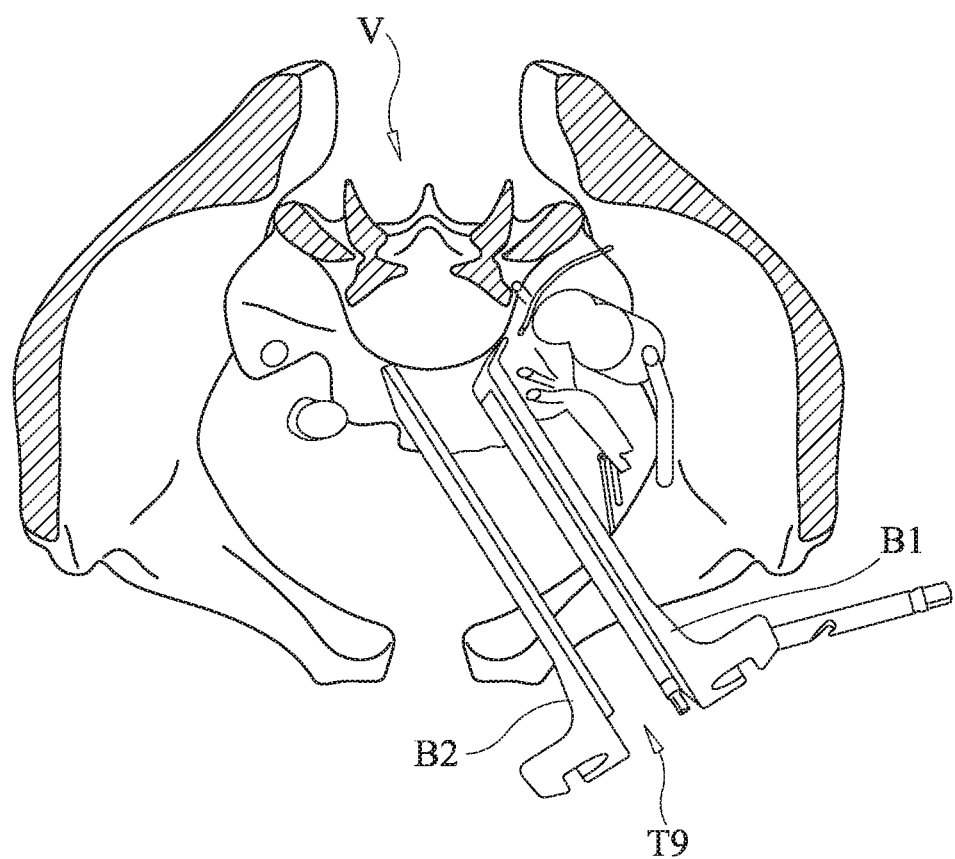
FIG. 13 is an axial view of the components and subject body shown in FIG. 12.
Figure 17:
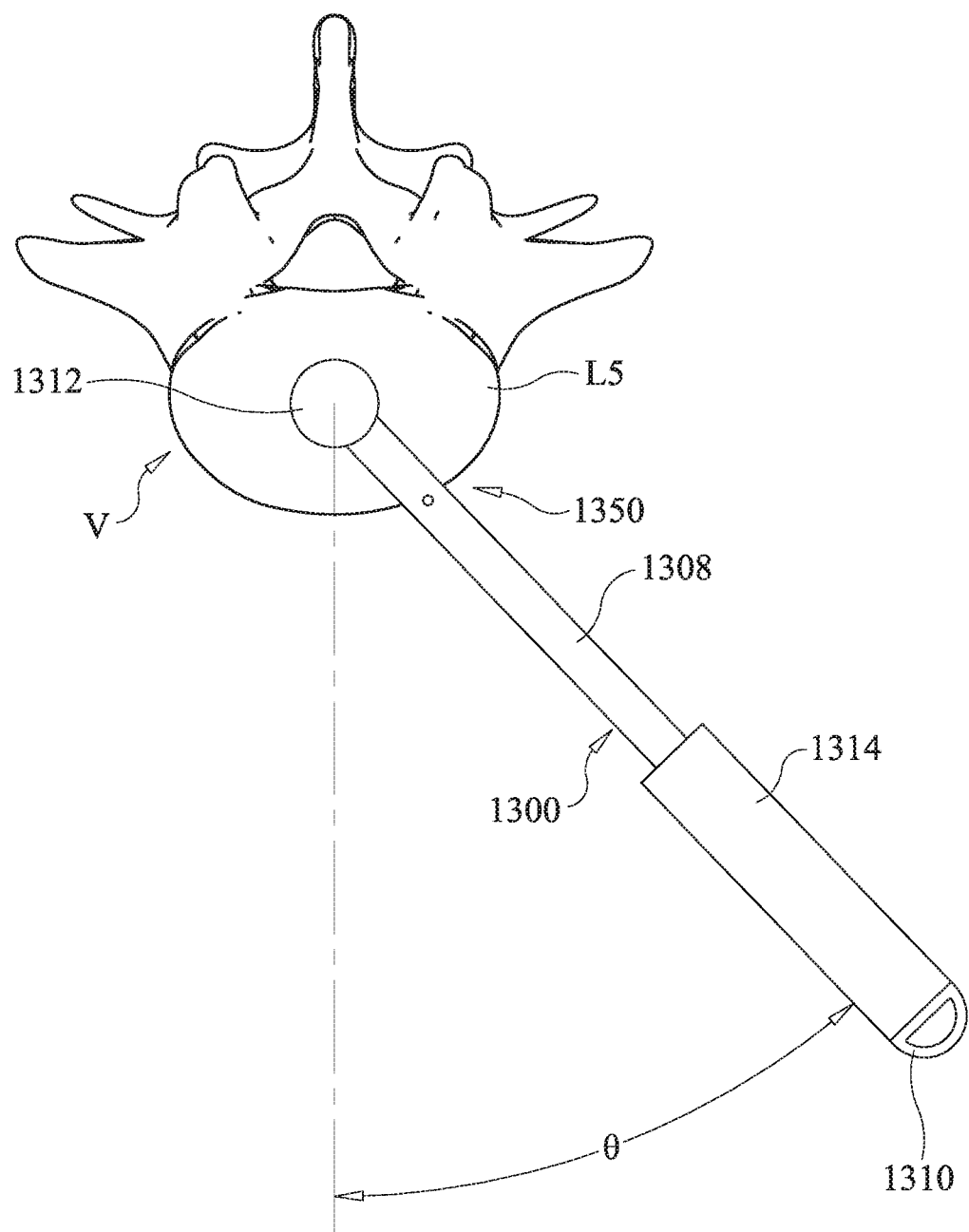
FIG. 17 is a plan view of components of one embodiment of a system in accordance with the principles of the present disclosure disposed with vertebrae.
Figure 18:
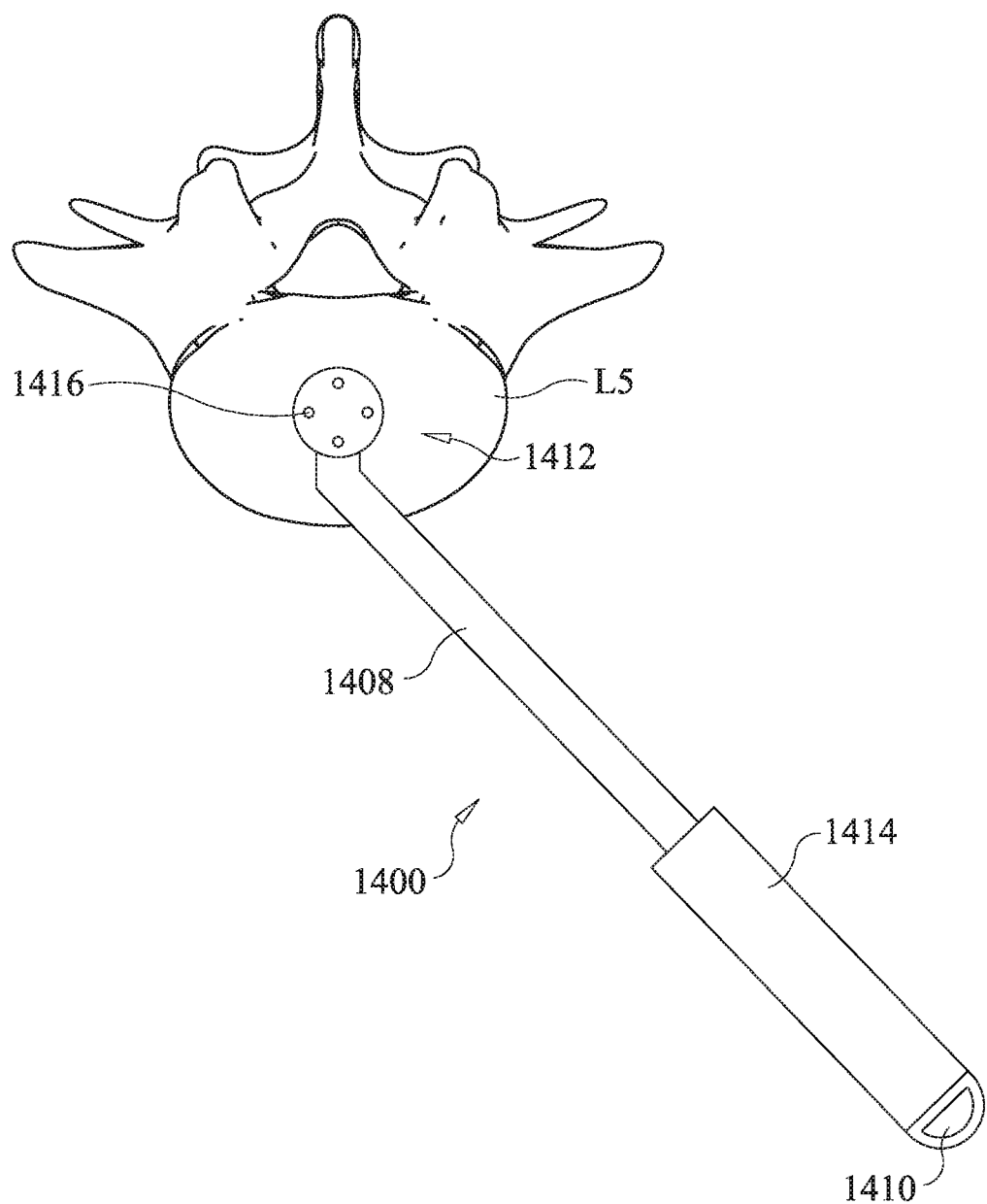
FIG. 18 is a plan view of components of one embodiment of a system in accordance with the principles of the present disclosure disposed with vertebrae.

In one embodiment, as shown in FIGS. 12, 12A and 13, system 10, similar to the systems and methods described herein, includes a surgical instrument, such as, for example, a retractor T9, which comprises blades B1, B2, B3 and can be manipulated and angled outside surgical pathway P. Blades B1, B2, B3 are disposed adjacent to the vessels, as described herein, and protects the surrounding vessels. For example, the blades B1, B2, B3 may be oriented and/or inserted independently or while selectively attached to a handheld inserter, see, for example, retractor T3, shown in FIGS. 4A and 4B. In other embodiments, the blades B1, B2, B3 may comprise blades 504, 506, 508, as shown in FIG. 6, wherein each blade is inserted separately, then manipulated into position relative to the anatomy, as shown in FIG. 12. The blades 504, 506, 508 may then to spread and/or held open using a retractor, see, for example, retractor T5 described with regard to FIGS. 5 and 6, with downward facing tips 500 that may be placed into holes 502. As shown in FIG. 12, in other embodiments, the blades B1, B2, B3 may also be left unattached to a frame or retractor system such that they remain unconstrained where the surgeon may manipulate each blade as necessary to maintain the operative corridor along an oblique angle while still allowing sufficient mobility of the blades to allow for instrument angulation to insert various trial instruments, for example, as shown in FIGS. 17 and 18, cages 12, for example, as shown in FIGS. 14-16 and 25-28, plates 132, for example, as shown in FIGS. 25-28), and fasteners 42, as shown, for example, in FIG. 16.

As shown in FIGS. 12, 12A and 13, the blades B1, B2, B3 may be positioned to maintain a safe surgical corridor near the aortic bifurcation BA and the inferior vena cava bifurcation BV. For example, blade B3 may be positioned to protect the bifurcations BA, BV themselves, while blades B1, B2 may be positioned an configured with angled distal tips to sweep away and maintain spacing of the bifurcated arterial and venous structures caudal to the bifurcations BA, BV.

In some embodiments, a discectomy is performed adjacent the L5-S1 intervertebral space via surgical pathway P. In some embodiments, sequential trial implants are delivered along surgical pathway P and used to distract the L5-S1 intervertebral space and apply appropriate tension in the L5-S1 intervertebral space allowing for indirect decompression. In some embodiments, the size of cage 12 is selected after trialing, cage 12 is visualized by fluoroscopy and oriented before malleting into the L5-S1 intervertebral space.

In some embodiments, trialing is utilized to establish a starting point for cage 12 insertion. In one embodiment, a trial instrument 1300, as shown in FIG. 17, includes a shaft 1308, a bubble level 1310 and a sphere 1312 that is inserted into the L5-S1 intervertebral space. An angle θ of trial instrument 1300 is adjusted via a handle 1314 until θ equals angle α (wherein angle α denotes a desired oblique angle of the surgical corridor as shown generally in FIGS. 14 and 15). Trial instrument 1300 is visualized radiographically and/or visually in the anterior plane and the lateral plane to adjust sphere 1312 position to a center of the disc space while maintaining angle θ. An intersection of shaft 1308 and the vertebral body is marked by point 1350. Marked point 1350 is a starting point for insertion of cage 12 at an angle θ. In some embodiments, marked point 1350 is aligned with a mark placed on the vertebral body, using a positioning trial instrument, such that the combination of matching the angle of the inserter, via the bubble level, and matching the mark on the vertebral body to marked point 1350 places cage 12 in a selected position, for example, as determined by the positioning trial instrument. In some embodiments, a practitioner centers cage 12 with the vertebral body, via, for example, radiographic markers, and aligns marked point 1350 with the mark on the vertebral body, which may negate the need for a complementary bubble level or inclinometer on an inserter instrument T10, such as those described herein with respect to FIGS. 19 and 20.

Figure 18A:
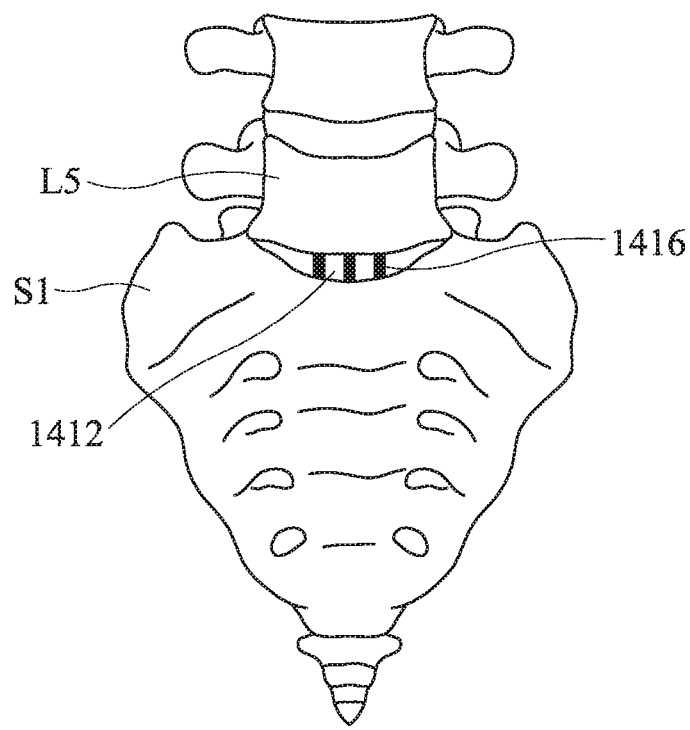
FIG. 18A is a side view of components and the vertebrae shown in FIG. 18.
Figure 18B:
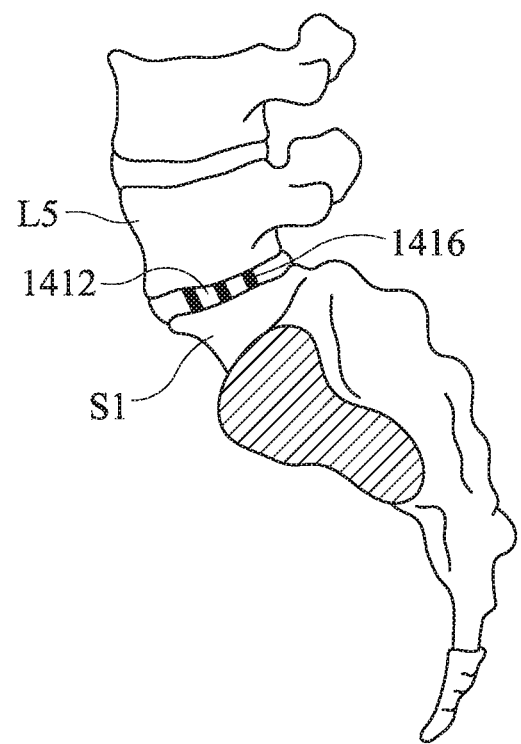
FIG. 18B is a side view of components and the vertebrae shown in FIG. 18.

In one embodiment, as shown in FIGS. 18, 18A and 18B, a trial instrument 1400, similar to trial instrument 1300 and methods of use described herein, includes an offset shaft 1408 connected to an offset handle 1414 and a cylinder 1412 that is inserted into the L5-S1 intervertebral space. Offset handle 1414 provides indicia of the offset of cage 12 insertion. Cylinder 1412 has a disc configuration and includes one or more, for example, four orthogonal radiopaque markers 1416 disposed circumferentially about cylinder 1412. In some embodiments, four orthogonal radiopaque markers 1416 include an anterior marker, a posterior marker, and a marker on each lateral border of cylinder 1412. In some embodiments, markers 1416 align shaft 1408 at a selected angle, such as angle α, for example, such that the markers 1416 are in the center of the L5-S1 intervertebral space as viewed from an AP and lateral view of medical imaging, such as those described herein, and near and far markers of cylinder 1412 are aligned and the position can be marked on the vertebral body for implant insertion.

In some embodiments utilizing cage 12 secured with fasteners 42, pilot holes or the like are made in selected vertebra L5 and S1 of vertebrae V adjacent the L5-S1 intervertebral space, via surgical pathway P, as shown for example, in FIG. 14, for receiving bone fasteners 42. Inserter T1 is attached with cage 12 adjacent oblique surface 44. Inserter T1 delivers cage 12 through incision I along surgical pathway P adjacent to a surgical site for implantation adjacent the L5-S1 intervertebral space. Anterior surface 14 faces an anterior side of body B adjacent anterior portion A1 and posterior surface 16 faces a posterior side of body B, as described herein. Surface 18 engages endplate tissue of endplate E1 and surface 20 engages endplate tissue of endplate E2.

Screw holes 24, 26 are oriented with the body of cage 12 in substantial alignment with surgical pathway P, as described herein. Screw hole 24 is oriented to receive a fastener 42a via surgical pathway P and is disposed at an angular orientation such that fastener 42a is delivered to the L5-S1 intervertebral space via surgical pathway P and oriented to penetrate endplate tissue of endplate E2, as shown in FIG. 15. Opening 46 guides fastener 42a into screw hole 24 relative to axis XB and in substantial alignment with surgical pathway P. Screw hole 26 is oriented to receive a fastener 42b via surgical pathway P and is disposed at an angular orientation such that fastener 42b is delivered to the L5-S1 intervertebral space via surgical pathway P and oriented to penetrate endplate tissue of endplate E1. Opening 48 guides fastener 42b into screw hole 26 relative to axis XB and in substantial alignment with surgical pathway P. A driver (not shown) is disposed adjacent the L5-S1 intervertebral space and is manipulated to drive, torque, insert or otherwise connect bone fasteners 42a, 42b adjacent the L5-S1 intervertebral space.

Upon completion of a procedure, as described herein, the surgical instruments, assemblies and non-implanted components of spinal implant system 10 are removed and the incision(s) are closed. One or more of the components of spinal implant system 10 can be made of radiolucent materials such as polymers. Radiopaque markers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal implant system 10. In some embodiments, spinal implant system 10 may include one or a plurality of plates, connectors and/or bone fasteners for use with a single vertebral level or a plurality of vertebral levels.

In one embodiment, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the components and/or surfaces of spinal implant system 10 with vertebrae. In some embodiments, the agent may include one or a plurality of therapeutic agents and/or pharmacological agents for release, including sustained release, to treat, for example, pain, inflammation and degeneration.

Figure 16:
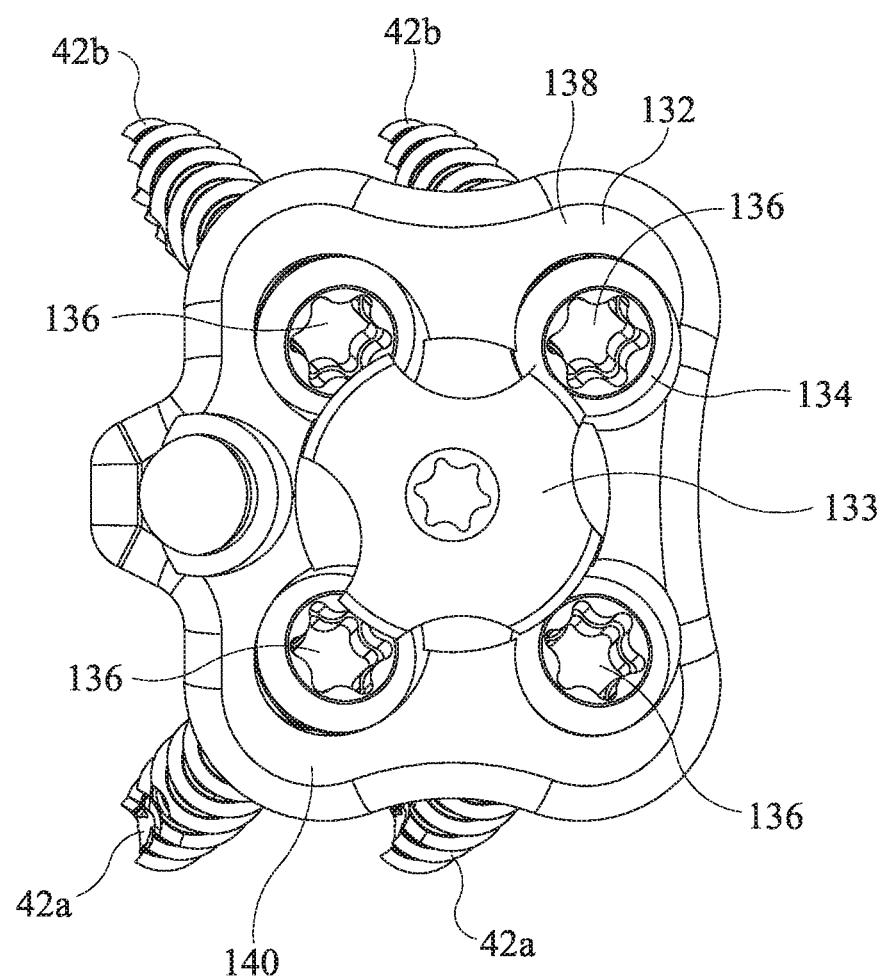
FIG. 16 is a perspective view of components of one embodiment of a system in accordance with the principles of the present disclosure.

One embodiment, as shown in FIG. 16, comprises a spinal construct including cage 12, described above, and a complementary plate 132 delivered through incision I along surgical pathway P adjacent to a surgical site for implantation adjacent the L5-S1 intervertebral space (FIG. 18). Plate 132 has a portion 138 configured to engage a vertebra, such as, for example, the L5 vertebra and a portion 140 configured to engage a vertebra, such as, for example, the S1 vertebra. In one embodiment, plate 132 may be attached with implant 12 prior to implantation or in situ. Plate 132 includes an inner surface 134 that defines openings 136 configured to receive fasteners 42, described herein. Fasteners 42a are configured for fixation with the S1 vertebra and fasteners 42b are configured for fixation with the L5 vertebra. In one embodiment, plate 132 is secured with implant 12 via a fastener. In some embodiments, plate 132 includes a back out prevention element 133.

In one embodiment, as shown in FIGS. 19-28, system 10, similar to the systems and methods described herein, comprises a spinal construct including cage 12 and plate 132, described above. Plate 132 includes a collet opening 160, as shown, for example, in FIGS. 25-28, configured for engagement with a surgical instrument, such as, for example, an inserter T10. Inserter T10 includes a body attachable to the spinal construct and a shaft connected with the body for manipulating the spinal construct.

Inserter T10 attaches to plate 132 at opening 160 via the components and/or mating parts of inserter T10 and the spinal construct to deliver plate 132 and/or cage 12 through incision I along surgical pathway P adjacent to a surgical site for implantation adjacent the L5-S1 intervertebral space.

Figure 19:
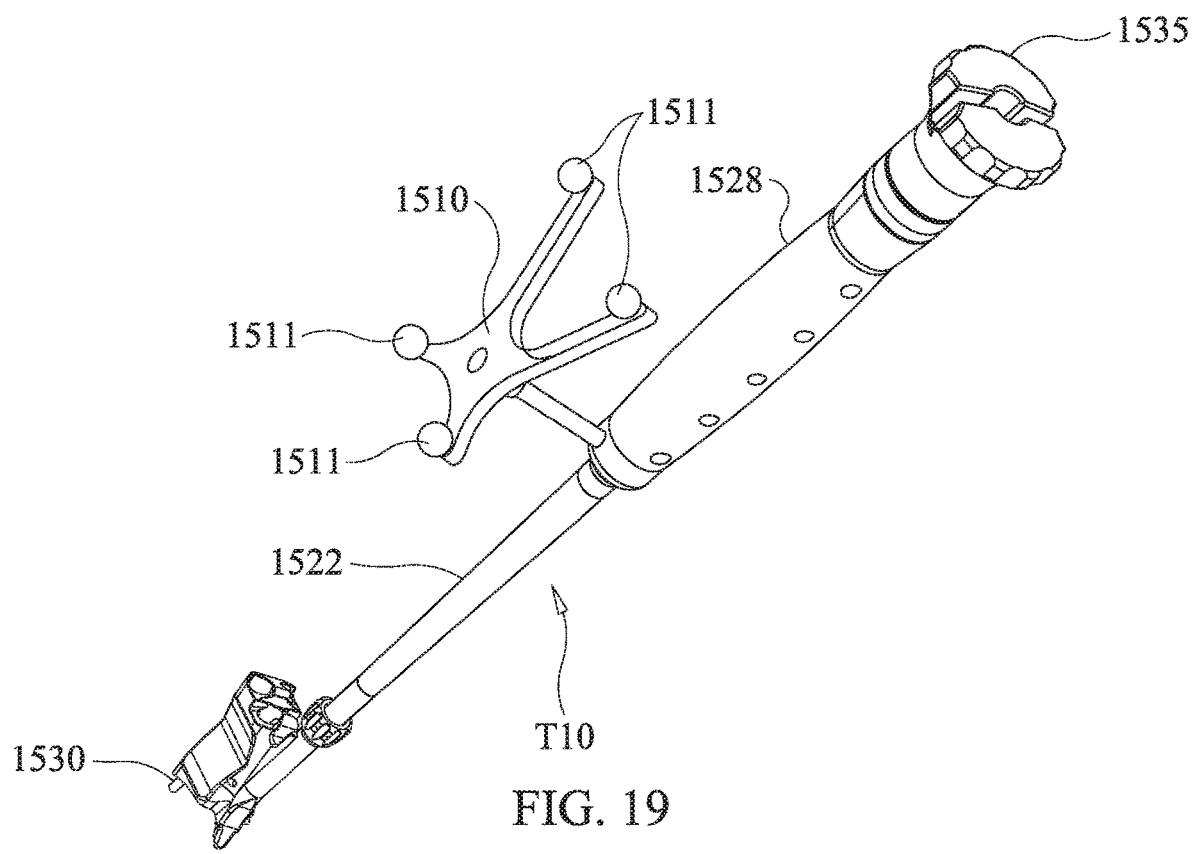
FIG. 19 is a perspective view of components of one embodiment of a system in accordance with the principles of the present disclosure.
Figure 20:
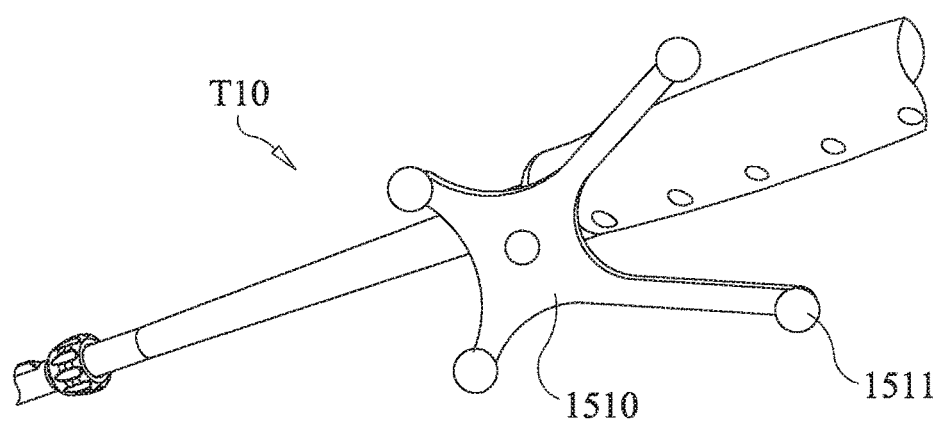
FIG. 20 is a perspective view of the components shown in FIG. 19.
Figure 21:
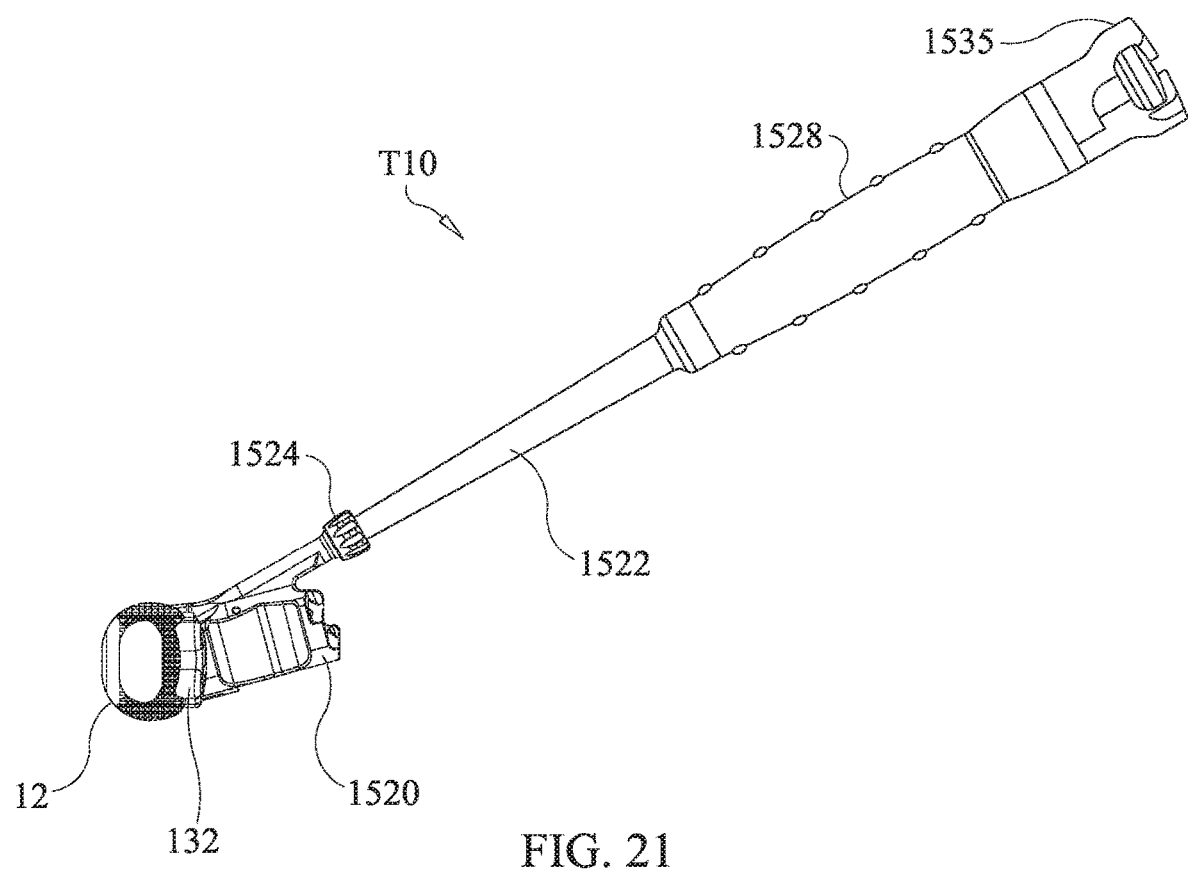
FIG. 21 is a side view of components of one embodiment of a system in accordance with the principles of the present disclosure.

In one embodiment, as shown in FIGS. 19 and 20, inserter T10 includes image guidance and/or surgical navigation to monitor, maintain, adjust and/or confirm disposal, delivery and/or alignment of the components of system 10 along surgical pathway P and/or adjacent to a surgical site. For example, the surgical navigation components of system 10 facilitate placement of cage 12 with the L5-S1 intervertebral space. The surgical navigation components of system 10 include an emitter 1510 configured to generate a signal representative of a position of inserter T10 and/or cage 12 connected therewith, for example, along surgical pathway P and/or adjacent to a surgical site such as the L5-S1 intervertebral space. In some embodiments, emitter 1510 may include one or a plurality of emitters. In one embodiment, emitter 1510 is shaped substantially like the Greek letter pi and comprises four spaced apart emitters 1511, for generating a signal representing the trajectory of inserter T10 and/or cage 12 relative to a portion of a patient's anatomy and the depth of inserter T10 and/or cage 12 along surgical pathway P and/or adjacent to a surgical site. In one embodiment, emitter 1510 includes at least one light emitting diode. In some embodiments, emitter 1510 may include other tracking devices capable of being tracked by a corresponding sensor array, such as, for example, a tracking device that actively generates acoustic signals, magnetic signals, electromagnetic signals, radiologic signals. In some embodiments, emitter 1510 may be removably attached to inserter T10. In some embodiments, emitter 1510 may be integrally formed with inserter T10 such that inserter T10 is a monolithic, unitary body.

In some embodiments, system 10 includes a tracking device (not shown) having an emitter array including one or a plurality of emitters that generate signals representing the position of various body reference points of the patient's anatomy. A sensor (not shown) receives signals from emitter 1510 and the array. The sensor communicates with a processor (not shown), such as, for example, a digitizer control unit, which processes the signals from emitter 1510 and the array to provide information regarding the trajectory of inserter T10 and/or cage 12 relative to a portion of the patient's anatomy and the depth of inserter T10 and/or cage 12 along surgical pathway P and/or adjacent to a surgical site. The processor sends this information to a monitor, which provides a visual representation of the position of inserter T10 and/or cage 12 along surgical pathway P and/or adjacent to a surgical site to allow the medical practitioner to guide inserter T10 and/or cage 12 to a desired location within the patient's anatomy.

The monitor is configured to generate an image from a data set stored in a controller, such as, for example, a computer. In some embodiments, the data set may be generated preoperatively using scanning techniques, such as, for example, a CAT scanner or MRI scanner. The image data set includes reference points for at least one body part, such as, for example, the spine of a patient, which has a fixed spatial relation to the body part. The processor is connected to the monitor, under control of the computer, and to inserter T10 and/or cage 12.

The sensor receives and triangulates signals generated by emitter 1510 and the array to identify the relative position of each of the reference points and inserter T10 and/or cage 12. The processor and the computer modify the image data set according to the identified relative position of each of the reference points during the procedure. The position and trajectory of inserter T10 and/or cage 12 provided by emitter 1510 and the array is processed by the processor and the computer and is visually displayed against the preoperative image data set stored in the computer to provide the medical practitioner with a visual representation of the trajectory of inserter T10 and/or cage 12 relative to a portion of the patient's anatomy and the depth of inserter T10 within the patient's anatomy. See, for example, similar surgical navigation components and their use as described in U.S. Pat. Nos. 6,021,343, 6,725,080, 6,796,988, the entire contents of each of these references being incorporated by reference herein.

Figure 22:
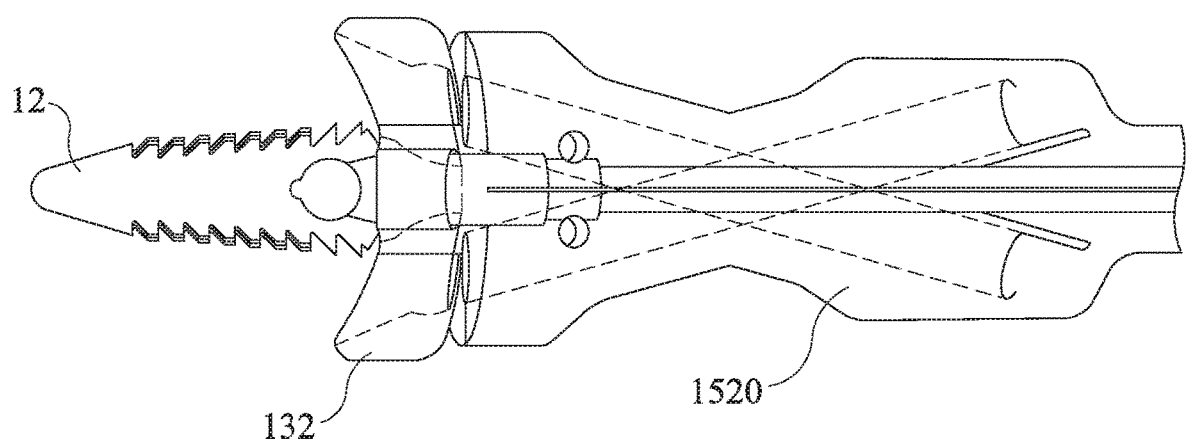
FIG. 22 is a detail side view of the components shown in FIG. 21.
Figure 23:
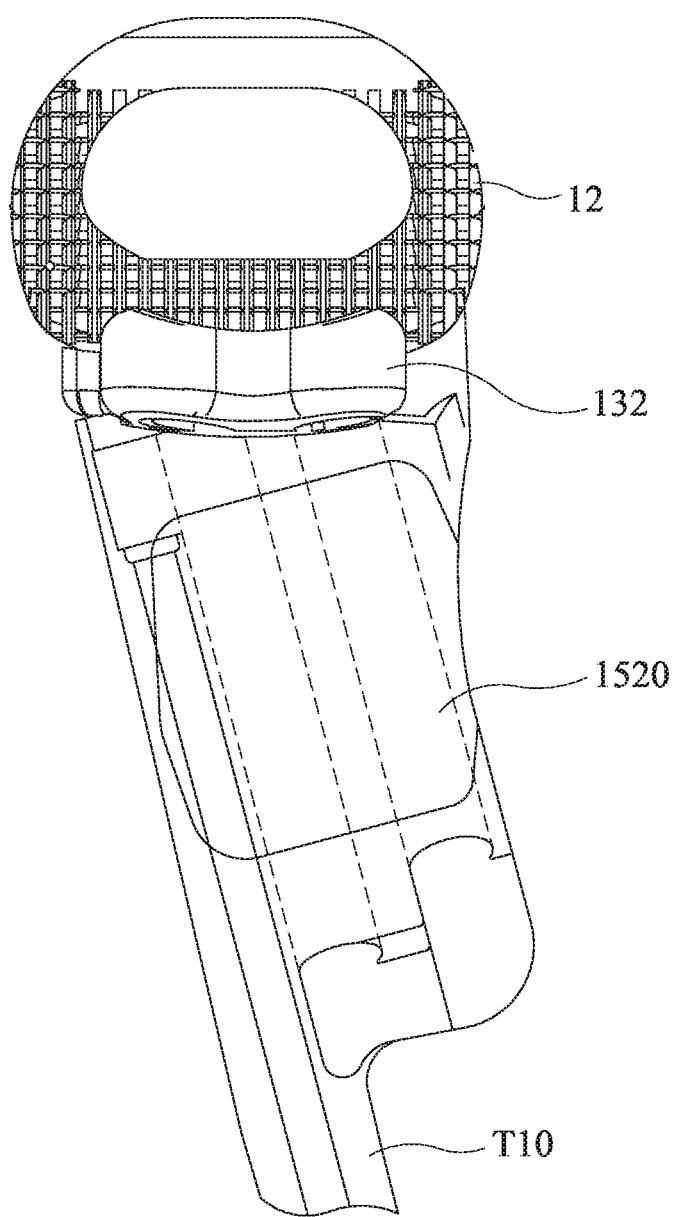
FIG. 23 is a detail top view of the components shown in FIG. 21.
Figure 24:
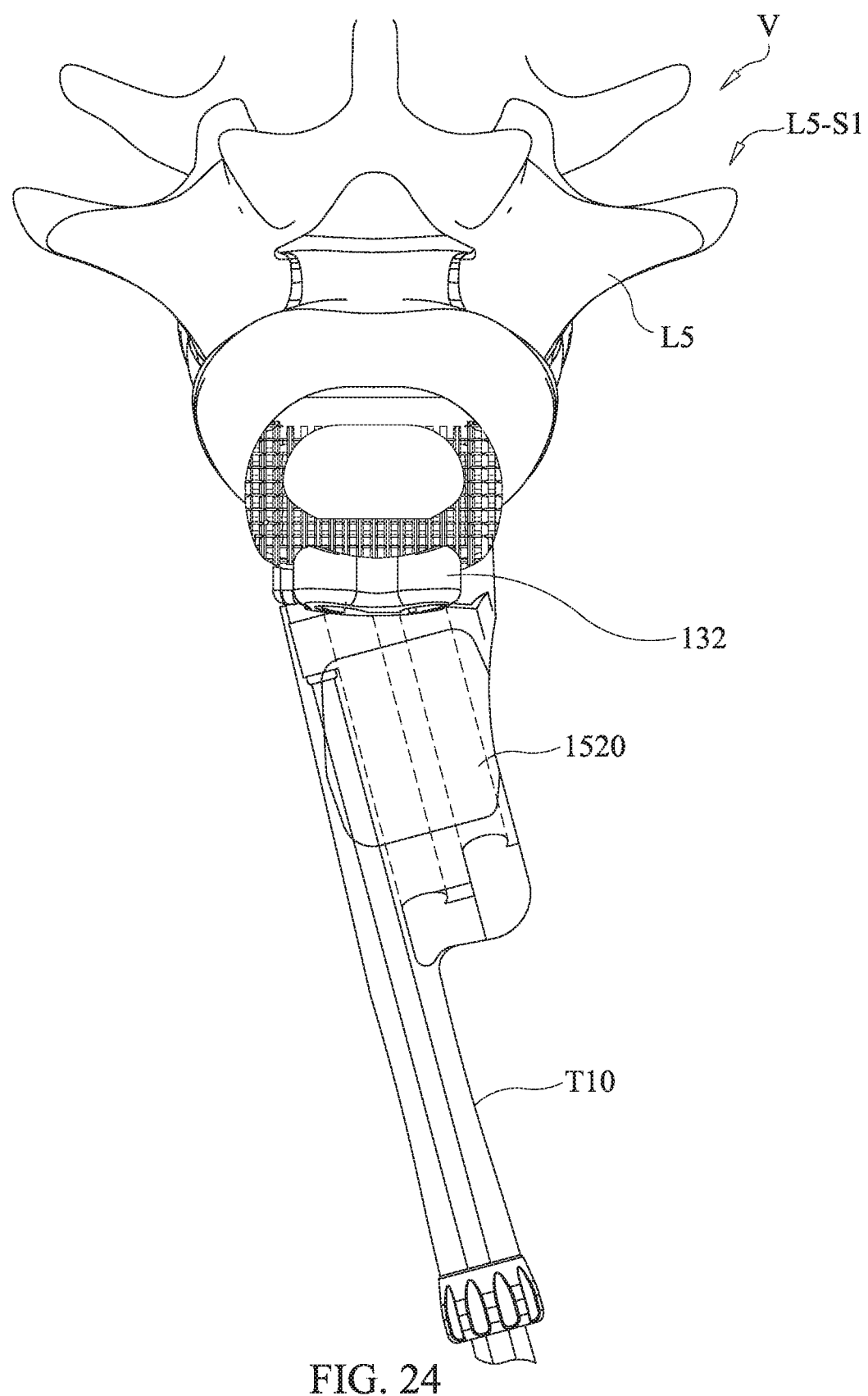
FIG. 24 is a detail top view of the components shown in FIG. 21 disposed with vertebrae.
Figure 25:
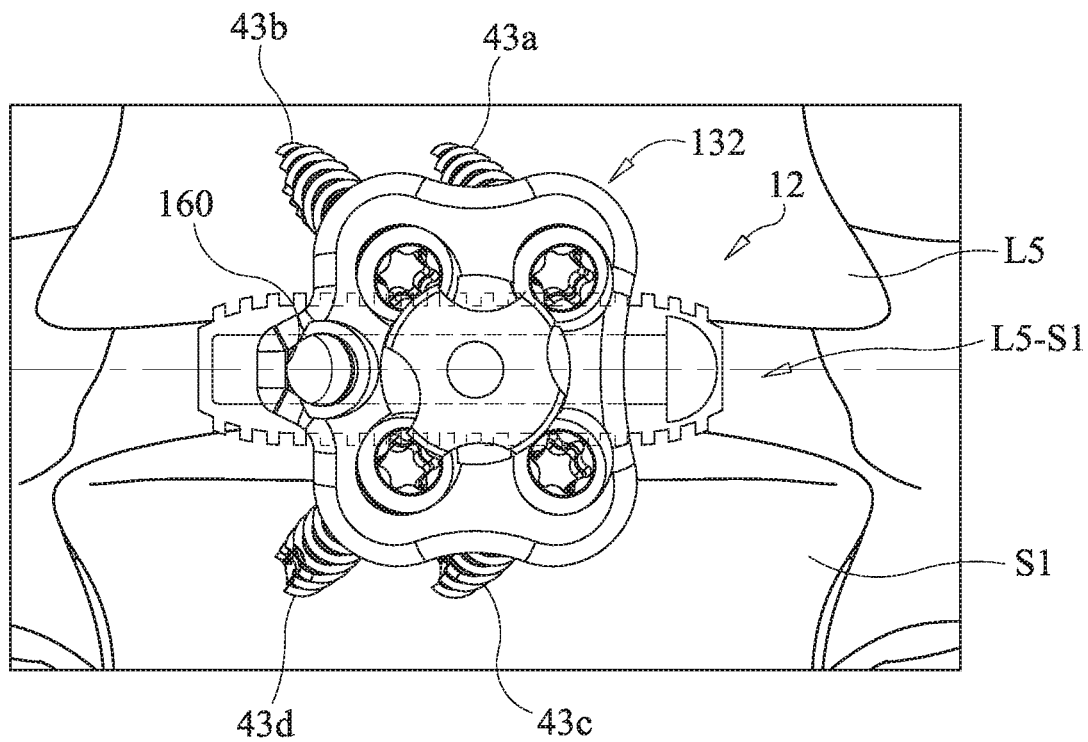
FIG. 25 is a side view of components of one embodiment of a system in accordance with the principles of the present disclosure disposed with vertebrae.
Figure 26:
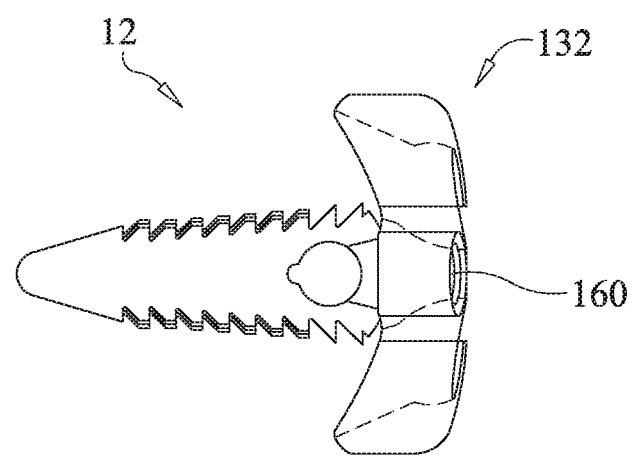
FIG. 26 is a side view of components of one embodiment of a system in accordance with the principles of the present disclosure.

In use, as shown in FIGS. 21-28, a modular drill, tap, and screw (DTS) guide 1520 mates with a shaft 1522 of inserter T10. Inserter T10 has a male protrusion that is aligned into a female connection on shaft 1522. A thread cap 1524 is manipulated to create a secure connection between shaft 1522 and DTS guide 1520. DTS guide 1520 is mated with cage 12 and plate 132, as shown in FIG. 22. The DTS guide 1520 may be provided in four-hole embodiments (see FIGS. 19-20, for example) for guiding drills, taps and screws for implanting a plate 132 and cage 12 embodiment. In such embodiments, the DTS guide may define holes or channels suitable for guiding fasteners 43a-43d (see FIG. 25) into the corresponding holes defined in the plate 132. In other embodiments, the DTS guide 1520 may comprise a two-hole embodiment (see FIG. 14, for example) suitable for guiding drills, taps and screws for implanting a cage-only embodiment. In such examples, as shown generally in FIG. 15, the fasteners 42a, 42b may comprise bone screws angled so as to enter the endplate E1 of either the sacrum S1 or the vertebral body V1.

In some embodiments, a specific size cage 12 and plate 132 are loaded into a loading block of system 10. Inserter T10 is placed onto plate 132 and into a side shelf on plate 132. An actuator 1526 of a handle 1528 is rotated clockwise to rigidly affix inserter T10, cage 12 and plate 132 together. Cage 12 and plate 132 can be delivered and implanted with the L5-S1 intervertebral space via inserter T10, as described above with regard to FIGS. 1-16.

Figure 27:
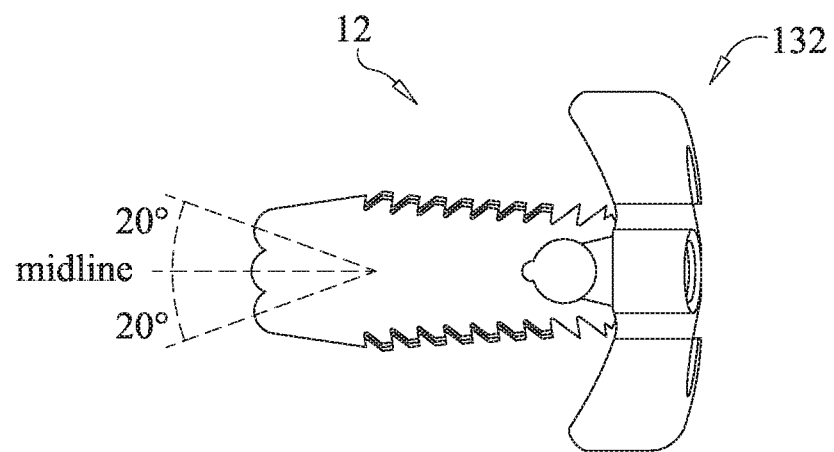
FIG. 27 is a side view of components of one embodiment of a system in accordance with the principles of the present disclosure.
Figure 27A:
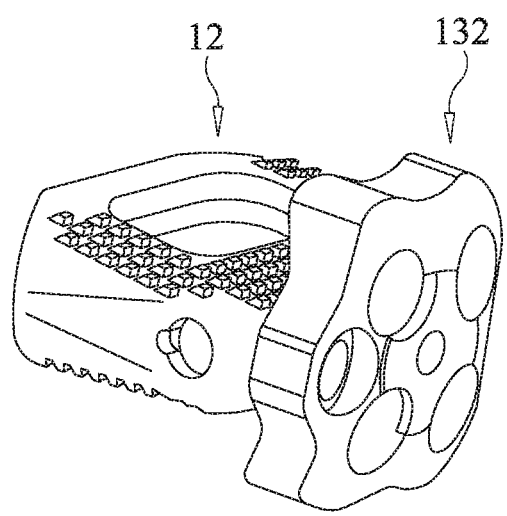
FIG. 27A is a perspective view of components of one embodiment of a system in accordance with the principles of the present disclosure.
Figure 28:
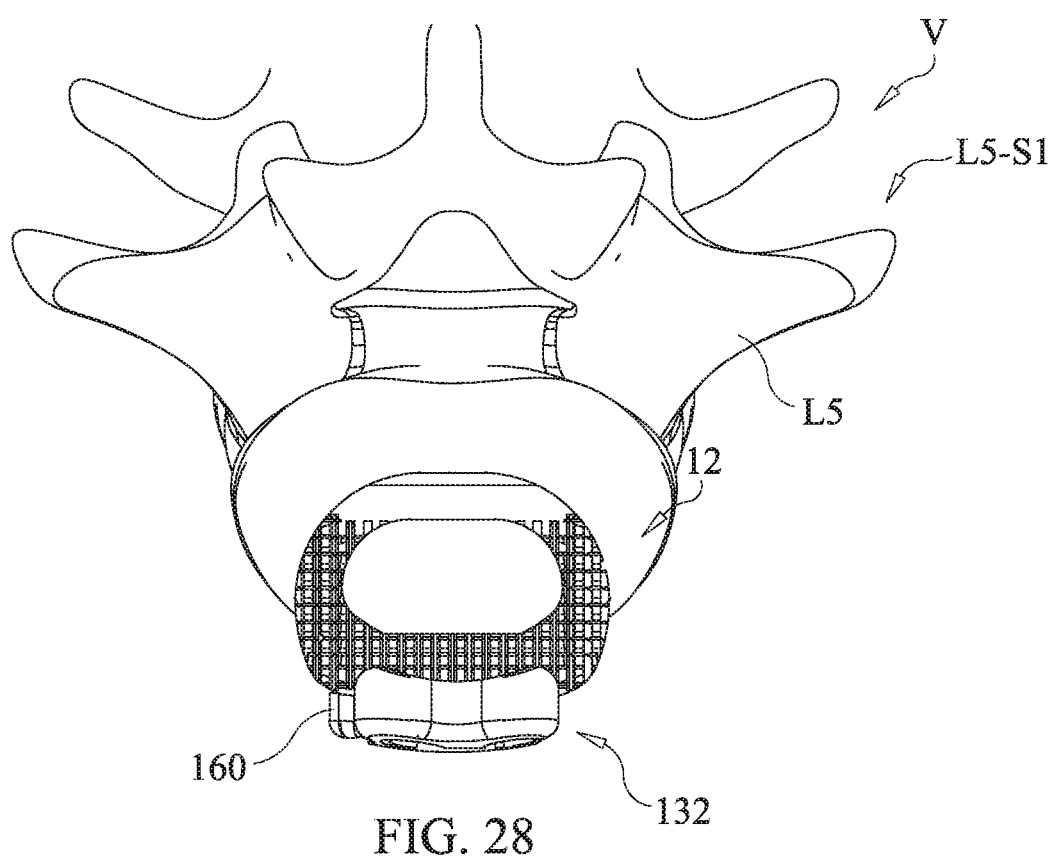
FIG. 28 is a plan view of components and vertebrae shown in FIG. 24.
Figure 29A:
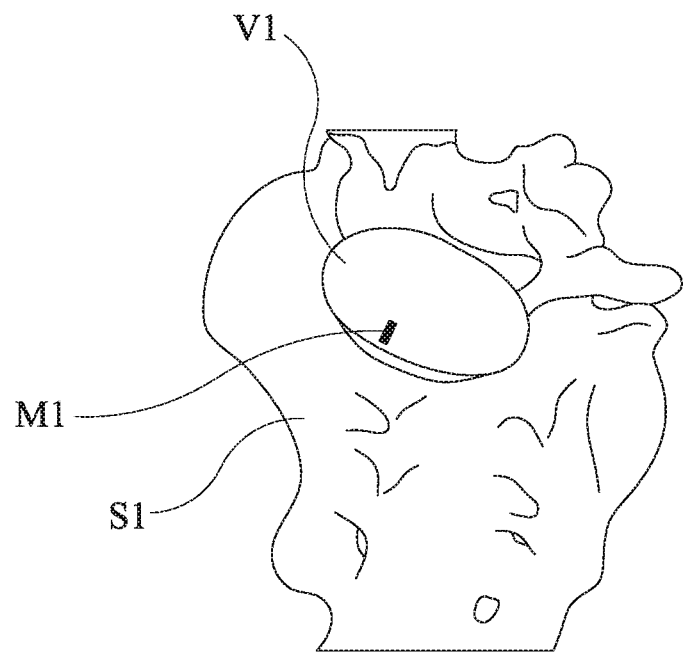
FIG. 29A is a perspective view of the L5-S1 level.
Figure 29B:
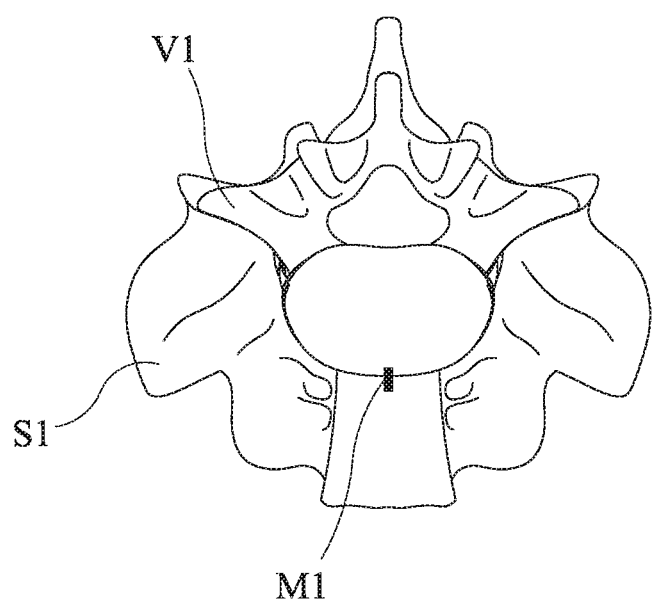
FIG. 29B is a plan view of the L5-S1 level.
Figure 30A:
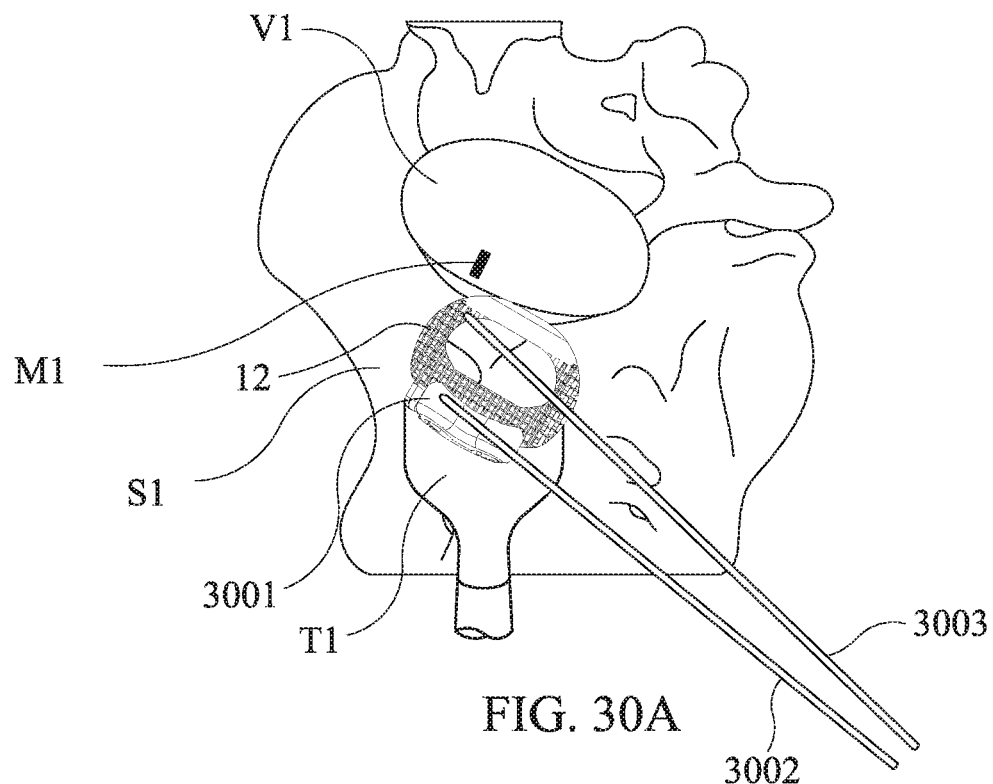
FIG. 30A is a perspective view of components of one embodiment of an inserter and cage in preparation for insertion according to one embodiment.
Figure 30B:
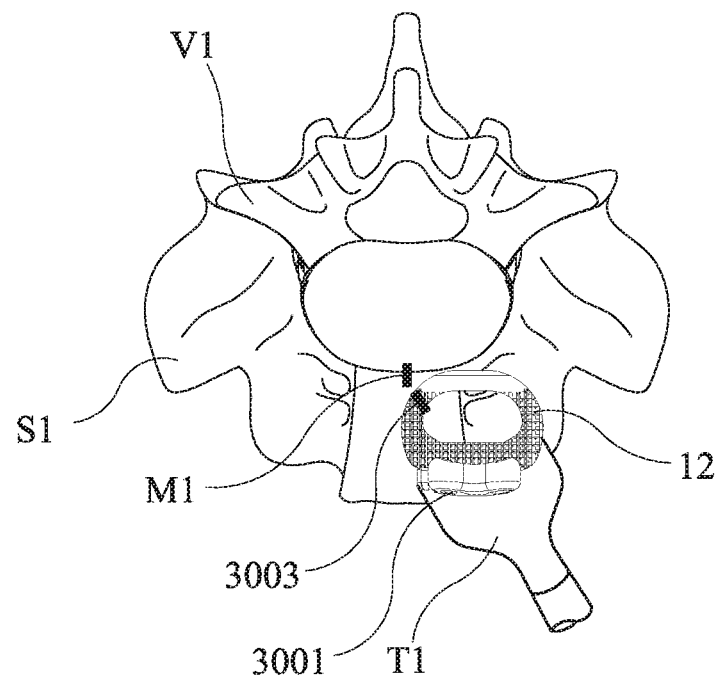
FIG. 30B is a plan view of components of one embodiment of an inserter and cage in preparation for insertion according to one embodiment.

In some embodiments, after implantation of cage 12 and plate 132, a practitioner can manipulate actuator 1526 counter clockwise to loosen the connection of T10, cage 12 and plate 132. This configuration allows plate 132 to toggle relative to cage 12, which provides cage 12 and plate 132 relative freedom of movement such that the practitioner can maneuver the spinal construct for final placement of cage 12 and/or plate 132. In some embodiments, plate 132 can rotate relative to cage 12 about an anterior face of cage 12 in a range of approximately 20 degrees, as shown in FIGS. 27 and 27A.

Inserter T10 is an adaptable instrument configured to perform multiple applications during a surgical procedure. In some embodiments, inserter T10 can prepare and/or create a cavity in tissue, such as, for example, bone. Inserter T10 guides a surgical instrument, such as, for example, a drill, tap and/or an awl, as well as guiding fasteners to penetrate tissue. In some embodiments, inserter T10 implants fasteners at an oblique angle with final placement centered on a midline of a sagittal plane. In some embodiments, inserter T10 is a guide that holds plate 132 and cage 12 together. Surgical instruments including an awl, a tap and screws are passed through inserter T10.

FIGS. 29A-31B show an alternative embodiment of the inserter T1 and cage 12 shown generally in FIGS. 14 and 15 in preparation for implantation in the intervertebral space between the sacrum S1 and the L5 vertebral body V1. In such embodiments, the inserter T1 may be modified from the embodiment shown in FIGS. 14 and 15 to include a stop element 3001. The stop element 3001 may comprise an extension from the inserter T1, providing a physical stop to prevent the inserter T1 from being over-inserted into the intervertebral space. As shown in FIG. 30A, the stop element 3001 may comprise a planar lateral surface 3002 placed so that the lateral surface 3002 may be used as a guide for properly aligning the implant for insertion along the oblique angle α (see FIGS. 14 and 15, for example and the description herein relative to FIGS. 30A and 30B). Furthermore, the cage 12 may be provided with an oblique marking 3003 on a contralateral side opposing the oblique insertion surface of the cage 12 that also serves as a visual guide to the surgeon for establishing and maintaining the oblique insertion pathway.

In such embodiments, a surgeon may make a midline mark M1, using a cauterizing or electrosurgical instrument (or other marking device) on the vertebral body V1 to mark the true midline of the vertebral body V1. Then, as shown generally in FIGS. 30A and 308, the surgeon may line up the oblique marking 3003 of the cage 12 with the midline mark M1 on the vertebral body V1. A proper oblique insertion pathway (see angle α shown in FIG. 14, for example) may then be established by visualizing an imaginary line from the oblique marking 3003 to the lateral surface 3002 of the stop element 3001. In some embodiments, a proximal (handle) end of the inserter T1 may also be fitted with an inclinometer or bubble level corresponding to a similar instrument (see element 1310 in FIG. 17) such that the oblique insertion pathway α may be established and/or verified by comparison to the angle α established using a trial 1300, 1400 (see FIGS. 17 and 18).

Figure 31A:
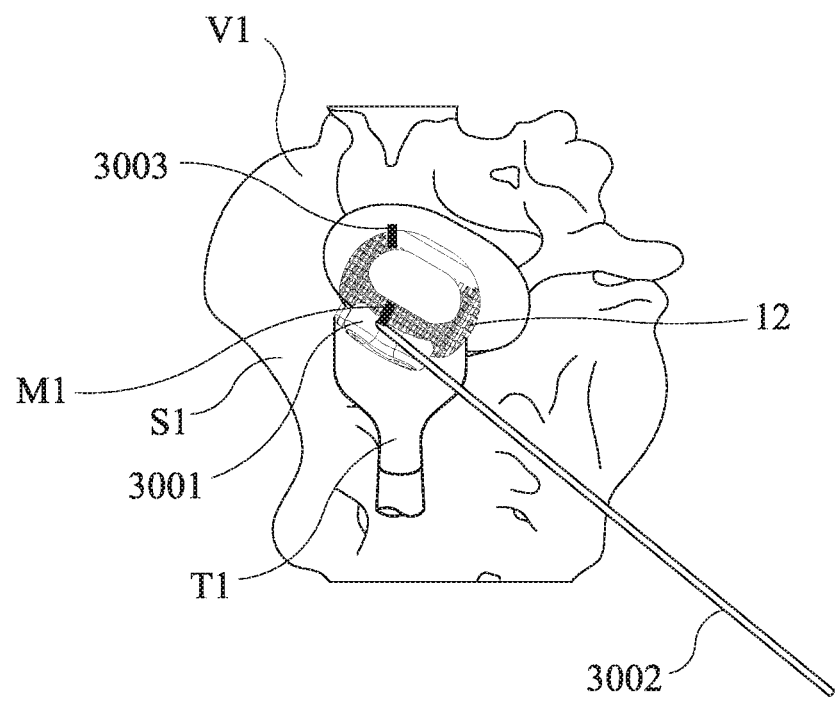
FIG. 31A is a perspective view of components of one embodiment of an inserter and cage in the final steps of insertion according to one embodiment.
Figure 31B:
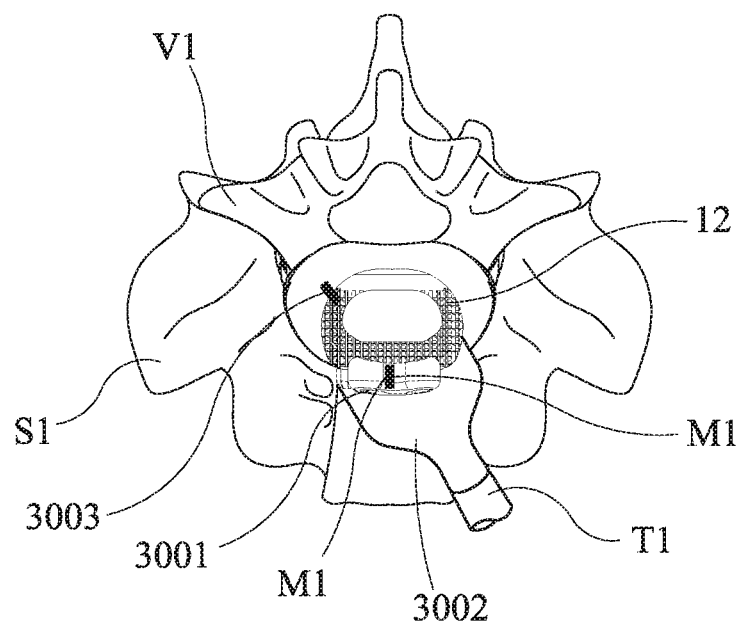
FIG. 31B is a plan view of components of one embodiment of an inserter and cage in the final steps of insertion according to one embodiment.

FIGS. 31A and 31B show the cage 12 fully seated in the intervertebral space between the sacrum S1 and the L5 vertebral body V1. When the cage 12 is fully seated in these embodiments, the midline mark M1 on the vertebral body V1 should line up with the lateral surface 3002 of the stop element 3001. Once the angle and orientation of the cage 12 is verified in this way, the inserter T1 may be disengaged (via disengagement of a threaded inserter rod as described further herein) from the cage 12 and retracted along the insertion pathway α. It should be understood that the various cage 12, inserter T1 and marking method (see M1) modifications described herein relative to FIGS. 29A-31B may also be applied to other cage and inserter embodiments described herein, including but not limited to the cage 12 and plate 132 embodiments of FIGS. 19-28.

It will be understood that various modifications may be made to the embodiments disclosed herein. Therefore, the above description should not be construed as limiting, but merely as exemplification of the various embodiments.

Those skilled in the art will envision other modifications within the scope and spirit of the claims appended hereto.

What is claimed is:

1. A surgical instrument comprising:
   a handle;
   a first member extending along a first longitudinal axis, the first member being connected to the handle by a pin that extends parallel to the first longitudinal axis, the first member comprising a track having a first section and a second section extending non-parallel relative to the first section, the pin being received in the second section, the first member being engageable with tissue of a substantially posterior portion of an incision relative to a body, the first member being rotatable relative to the handle about the first longitudinal axis;
   a second member connected with the handle and extending along a second longitudinal axis that extends parallel to the first longitudinal axis, the second member being engageable with tissue of a substantially anterior portion of the incision relative to the body, the second member being rotatable relative to the handle about the second longitudinal axis, the first and second members being rotatable relative to one another about a pivot axis that extends parallel to the first and second longitudinal axes; and
   a third member connected with the handle and engageable with tissue of a substantially cephalad portion of the incision relative to the body,
   the members being disposable in a configuration to space the tissue to define an oblique surgical pathway relative to a bilateral axis of the body.

2. A surgical instrument as recited in claim 1, wherein each of the members includes an axial cavity configured for disposal of a pin engageable with bone adjacent the pathway to fix the members relative to the bone.

3. A surgical instrument as recited in claim 1, wherein at least one of the members includes spaced axial cavities.

4. A surgical instrument as recited in claim 1, wherein the handle includes arms that are independently connected with the first and second members to rotate the first and second members about the pivot axis.

5. A surgical instrument as recited in claim 4, wherein the pin is fixed relative to one of the arms.

6. A surgical instrument as recited in claim 4, wherein each of the arms is independently movable such that the members can be independently and selectively movable relative to the other members.

7. A surgical instrument as recited in claim 4, wherein the first and second members are relatively and selectively movable in a substantially anterior-posterior direction.

8. A surgical instrument as recited in claim 4, wherein the third member is selectively movable in a substantially cephalad direction relative to the first and second members.

9. A surgical instrument as recited in claim 1, wherein the handle includes a ratchet.

10. A surgical instrument as recited in claim 1, wherein at least one of the members includes a distal curvature.

11. A surgical instrument as recited in claim 1, wherein at least one of the members includes a sensor for detecting and/or measuring vascular data.

12. A surgical instrument as recited in claim 1, wherein at least a portion of at least one of the members is translucent.

13. A surgical instrument as recited in claim 1, wherein the handle comprises first and second arms that are connected to the first and second members and a third arm that is connected to the third member, the third arm extending through the pivot axis.

14. A surgical instrument as recited in claim 13, wherein the third arm defines a slide axis that extends perpendicular to the pivot axis, the third arm being configured to move in opposite directions along the slide axis to move the third member relative to the first and second members.

15. A surgical instrument as recited in claim 14, wherein the third arm extends through a ratcheting slide of the handle that is configured to prevent movement of the third arm along the slide axis.

16. A surgical instrument as recited in claim 13, wherein the handle includes a ratcheting mechanism that is fixed to the first arm and extends through the second arm, the ratcheting mechanism being configured to prevent rotation of the first member relative to the second member.

17. A surgical instrument as recited in claim 1, wherein the members each include a channel that extends parallel to the longitudinal axes through opposite top and bottom surfaces of the members.

18. A surgical instrument comprising:
    a handle;
    a posterior blade connected with the handle and extending along a first longitudinal axis, the posterior blade being connected to the handle by a first pin that extends parallel to the first longitudinal axis, the posterior blade comprising a recessed track having a first section and a second section extending at a right angle relative to the first section, the second section being in communication with the first section, the first pin being received in the second section, the posterior blade being rotatable relative to the handle about the first longitudinal axis;
    an anterior blade connected with the handle and extending along a second longitudinal axis that extends parallel to the first longitudinal axis, the anterior blade being connected to the handle by a second pin that extends parallel to the second longitudinal axis, the second pin being received in a recess of the anterior blade, the anterior blade being rotatable relative to the handle about the second longitudinal axis, the blades being rotatable relative to one another about a pivot axis that extends parallel to the first and second longitudinal axes; and
    a cephalad blade connected with the handle,
    wherein the blades are disposable in a configuration to space tissue of an incision to define an oblique surgical pathway relative to a bilateral axis of a body.

19. A surgical instrument as recited in claim 18, wherein the handle is independently connected with the blades such that each of the blades can be independently and selectively movable relative to the other blades.

20. A surgical instrument comprising:
    a handle having a first arm comprising a first pin, a second arm comprising a second pin and a third arm comprising a third pin, the first and second arms being rotatable relative to one another about a pivot axis, the third arm being slidable relative to the first arm and the second arm;
    a posterior blade extending along a first longitudinal axis and comprising a first recessed track having a first section and a second section extending at a ninety degree angle relative to the first section, the second section being in communication with the first section, the first pin being received in the second section to couple the posterior blade to the handle, the posterior blade being rotatable relative to the first pin about the first longitudinal axis;
    an anterior blade extending along a second longitudinal axis and comprising a second recessed track having a first section and a second section extending at a ninety degree angle relative to the first section of the second track, the second section of the second track being in communication with the first section of the second track, the second pin being received in the second section of the second track to couple the anterior blade to the handle, the anterior blade being rotatable relative to the second pin about the second longitudinal axis; and a cephalad blade positioned between the posterior blade and the anterior blade, the cephalad blade defining a third longitudinal axis, the cephalad blade comprising a third recessed track having a first section and a second section extending at a ninety degree angle relative to the first section of the third track, the second section of the third track being in communication with the first section of the third track, the third pin being received in the second section of the third track to couple the cephalad blade to the handle, the cephalad blade being rotatable relative to the third pin about the third longitudinal axis, wherein the blades are disposable in a configuration to space tissue of an incision to define an oblique surgical pathway relative to a bilateral axis of a body.

* * * * *